[12] United States Patent
Brenner et al.

(10) Patent No.: US 9,845,493 B2
(45) Date of Patent: Dec. 19, 2017

(54) TUNABLE FLUORESCENCE USING CLEAVABLE LINKERS

(71) Applicant: Agency for Science, Technology and Research, Singapore (SG)

(72) Inventors: Sydney Brenner, Singapore (SG); Yin Nah Teo, Singapore (SG); Pee Mei Tan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/784,939

(22) PCT Filed: Apr. 21, 2014

(86) PCT No.: PCT/SG2014/000175
§ 371 (c)(1),
(2) Date: Oct. 15, 2015

(87) PCT Pub. No.: WO2014/171899
PCT Pub. Date: Oct. 23, 2014

(65) Prior Publication Data
US 2016/0145280 A1    May 26, 2016

Related U.S. Application Data

(60) Provisional application No. 61/813,694, filed on Apr. 19, 2013.

(51) Int. Cl.
*C12Q 1/68* (2006.01)
*C07H 19/04* (2006.01)
(Continued)

(52) U.S. Cl.
CPC ......... *C12Q 1/6818* (2013.01); *C07D 207/46* (2013.01); *C07D 493/10* (2013.01);
(Continued)

(58) Field of Classification Search
CPC .. C12Q 1/6818; G01N 21/6428; C09B 11/08; C09B 23/006; C09B 29/0003; C07H 21/04
(Continued)

(56) References Cited

U.S. PATENT DOCUMENTS 5,141,813 A * 8/1992 Nelson .................. C07H 21/00
428/402
5,451,463 A * 9/1995 Nelson .................. C07H 21/00
428/402
(Continued)

FOREIGN PATENT DOCUMENTS

WO    2007109364 A2    9/2007

OTHER PUBLICATIONS

International Preliminary Report on Patentability for International Application No. PCT/SG2014/000175 dated Oct. 20, 2015, pp. 1-7.
(Continued)

*Primary Examiner* — Jezia Riley
(74) *Attorney, Agent, or Firm* — Winstead, P.C.

(57) ABSTRACT

The invention relates to cleavable chemistry in general, and in particular, to tunable fluorescence using cleavable linkers present in fluorochrome-quencher conjugates.

23 Claims, 7 Drawing Sheets

(51) Int. Cl.
| | |
|---|---|
| C09B 29/01 | (2006.01) |
| C09B 23/06 | (2006.01) |
| C09B 11/08 | (2006.01) |
| C07H 21/04 | (2006.01) |
| C07D 493/10 | (2006.01) |
| C07D 207/46 | (2006.01) |
| C07F 9/655 | (2006.01) |
| C07F 9/6561 | (2006.01) |
| C07F 9/165 | (2006.01) |
| C07F 9/24 | (2006.01) |
| C07F 7/12 | (2006.01) |
| C07F 7/18 | (2006.01) |
| G01N 21/64 | (2006.01) |

(52) U.S. Cl.
CPC ............ *C07F 7/12* (2013.01); *C07F 7/184* (2013.01); *C07F 9/1651* (2013.01); *C07F 9/2408* (2013.01); *C07F 9/6561* (2013.01); *C07F 9/65522* (2013.01); *C07F 9/65616* (2013.01); *C07H 21/04* (2013.01); *C09B 11/08* (2013.01); *C09B 23/06* (2013.01); *C09B 29/0003* (2013.01); *G01N 21/6428* (2013.01); *G01N 2021/6432* (2013.01); *G01N 2021/6439* (2013.01); *G01N 2201/068* (2013.01)

(58) Field of Classification Search
USPC .......................................... 435/6.1; 536/26.6
See application file for complete search history.

(56) References Cited

U.S. PATENT DOCUMENTS

| | | | | |
|---|---|---|---|---|
| 5,512,667 | A * | 4/1996 | Reed ................... | C07D 207/12 536/24.3 |
| 5,585,422 | A * | 12/1996 | Falk .................... | C07D 403/10 524/100 |
| 5,696,251 | A * | 12/1997 | Arnold, Jr. ............ | C07H 21/00 536/23.1 |
| 6,031,091 | A * | 2/2000 | Arnold, Jr. ............ | C07F 9/2408 536/23.1 |
| 6,790,945 | B2 * | 9/2004 | Lukhtanov ............ | C07C 245/08 435/6.1 |
| 2006/0160081 | A1 | 7/2006 | Milton et al. | |
| 2007/0042407 | A1 | 2/2007 | Milton et al. | |
| 2009/0259030 | A1 | 10/2009 | Cook et al. | |
| 2009/0263791 | A1 | 10/2009 | Ju et al. | |
| 2010/0292452 | A1 | 11/2010 | Milton et al. | |
| 2010/0304368 | A1 | 12/2010 | Cherkasov et al. | |
| 2014/0113322 | A1 * | 4/2014 | Cui ..................... | G01N 33/542 435/23 |

OTHER PUBLICATIONS

Haugland, R.P., "The Handbook—A Guide to Fluorescent Probes and Labeling Technologies," Invitrogen Corp., 10th ed., 2005, https://www.thermofisher.com/sg/en/home/references/molecular-probes-the-handbook.html, pp. 1-1126, see Chapter 1: Fluorophores and Their Amine-Reactive Derivatives, pp. 11-97.

Conchello et al., "Optical Sectioning Microscopy," Nat Methods, vol. 2 No. 12, Dec. 2005, pp. 920-931.

Lichtman et al., "Fluorescence Microscopy," Nat Methods, vol. 2 No. 12, Dec. 2005, pp. 910-919.

Shendure et al., "Next-Generation DNA Sequencing," Nat. Biotechnol, vol. 26 No. 10, Oct. 2008, pp. 1135-1145.

Guo et al., "An Integrated System for DNA Sequencing by Synthesis Using Novel Nucleotide Analogues," Acc. Chem. Res., vol. 43 No. 4, Apr. 20, 2010, pp. 551-563.

Li et al., "A Photocleavable Fluorescent Nucleotide for DNA Sequencing and Analysis," P. Natl. Acad. Sci. U.S.A., vol. 100, No. 2, Jan. 21, 2003, pp. 414-419.

Seo et al., "Photocleavable Fluorescent Nucleotides for DNA Sequencing on a Chip Constructed by Site-Specific Coupling Chemistry," P. Natl. Acad. Sci. U.S.A., vol. 101, No. 15, Apr. 13, 2004, pp. 5488-5493.

Seo et al., "Four-Color DNA Sequencing by Synthesis on a Chip Using Photocleavable Fluorescent Nucleotides," P. Natl. Acad. Sci. U.S.A., vol. 102, No. 17, Apr. 26, 2005, pp. 5926-5931.

Ju et al., "Four-Color DNA Sequencing by Synthesis Using Cleavable Fluorescent Nucleotide Reversible Terminators," Proc Natl Acad Sci USA, vol. 103, No. 52, Dec. 26, 2006, pp. 19635-19640.

Guo et al., "Four-Color DNA Sequencing with 3'-O-Modified Nucleotide Reversible Terminators and Chemically Dleavable Fluorescent Dideoxynucleotides," P. Natl. Acad. Sci. U.S.A., vol. 105, No. 27, Jul. 8, 2008, pp. 9145-9150.

Bentley et al., "Accurate Whole Human Genome Sequencing Using Reversible Terminator Chemistry," Nature, vol. 456, No. 7218, Nov. 6, 2008, pp. 53-59.

Bowers et al., "Virtual Terminator Nucleotides for Next-Generation DNA Sequencing," Nat Methods, vol. 6, No. 8, Aug. 2009, pp. 593-595.

Drmanac et al., "Human Genome Sequencing Using Unchained Base Reads on Self-Assembling DNA Nanoarrays," Science, vol. 327, No. 5961, Jan. 1, 2010, pp. 78-81.

Shendure et al., "Accurate Multiplex Polony Sequencing of an Evolved Bacterial Genome," Science, vol. 309, No. 5741, Sep. 9, 2005, pp. 1728-1732.

McKernan et al., "Sequence and Structural Variation in a Human Genome Uncovered by Short-Read, Massively Parallel Ligation Sequencing Using Two-Base Encoding," Genome Res, vol. 19, No. 9, 2009, pp. 1527-1541.

Sasson et al., "Filtering Error From SOLiD Output," Bioinformatics, vol. 26, No. 6, 2010, pp. 849-850.

Zhou et al., "Synthesis of Dendritic Trypsin Sensors," Polymer Preprints, vol. 51 No. 1, 2010, pp. 674-675, https://science.williams.edu/wp-content/blogs.dir/72/files/RS10html/ros2010-FACULTY.html, see Abstract.

Sloniec et al., "Photophysics and Release Kinetics of Enzyme-Activatable Optical Probes Based on H-Dimerized Fluorophores on Self-Immolative Linkers," J Phy Chem B, vol. 117, 2013, pp. 14336-14344.

Zhou et al., "Synthesis of Dendritic Trypsin Sensors," Polymer Preprints, 2010, 51(1), pp. 674-675.

Written Opinion for International Application No. PCT/SG2014/000175 dated May 27, 2014, pp. 1-11.

\* cited by examiner

Point of attachment
to DNA, peptide or protein

Azido linker  Allyl linker  Disulfide linker

Phosphorothioate linker  Diol linker  Diazobenzene linker

Acylsulfonamide linker  Silyl linker

| Linkers (10mM) | Cleavage reagents |
| --- | --- |
| Diol | 15mM NaIO$_4$ |
| Phosphothioate | 50mM AgNO$_3$ |
| Disulfide | 20mM DTT (Dithiothreitol) |
| Silyl | 60mM TBAF/THF |

Fluorophores

| Fluorophores | $\lambda_{EX}$ (nm) | $\lambda_{EM}$ (nm) |
|---|---|---|
| 5(6)carboxyfluorescein | 494 | 518 |
| BODIPY | 503 | 512 |
| 1-pyrenebutyric acid | 340 | 470 |

Fluorophores

| Fluorophores | $\lambda_{EX}$ (nm) | $\lambda_{EM}$ (nm) |
|---|---|---|
| Cy3 NHS ester | 555 | 570 |
| 7-diethylaminocoumarin-3-carboxylic acid | 350 | 470 |

Quencher

Dabcyl
- Excitation wavelength 498nm

PM2_24 (Si-Py-Oligo-SS-Dab)

TUNABLE FLUORESCENCE USING CLEAVABLE LINKERS

CROSS-REFERENCE TO RELATED APPLICATION

This application claims the benefit of priority of U.S. Provisional Patent Application No. 61/813,694, filed Apr. 19, 2013, the contents of which being hereby incorporated by reference in its entirety for all purposes.

TECHNICAL FIELD

The invention relates to cleavable chemistry in general, and in particular, to tunable fluorescence using cleavable linkers present in fluorochrome-quencher conjugates.

BACKGROUND

The ability to visualize multiple biological interactions using fluorescence depends on the availability of spectrally well-defined fluorophores. This is a challenge for currently available fluorophores as most of them exhibit broad excitation and emission spectrum. Thus, overlapping of emission signals lead to bleed though between detection channels and loss of accuracy in detection. In addition, the visible spectrum only stretches across 300 nm, placing a further limitation on the number of fluorophores that can be optically resolved within this range.

Therefore, there remains a need to provide for greater ease and simplicity for fluorescence detection of biomolecules.

SUMMARY

Adding cleavable quenchers to fluorochromes, such as fluorophores, allows one to tune their fluorescence and release it only upon addition of a cleaving reagent. In addition to the fluorophore's emission properties, an addition variable is added—cleavage reagent, thus increasing their diversity. This can be particularly useful in applications where increasing the number of probes increases throughput and efficiency.

The use of cleavable quenchers in combination with cleavable fluorochromes through orthogonal chemistries can increase the number of fluorochromes that can be used in such a sequencing-by-ligation application. Direct dinucleotide interrogation with 16 possible combinations can be carried out using 4 dyes and 5 orthogonal cleavable chemistries.

Accordingly, a first aspect of the invention relates to a fluorochrome-quencher conjugate having the structure

F-L1-B-L2-Q wherein
F is at least one fluorochrome;
Q is at least one quenching molecule for the at least one fluorochrome, or is another fluorochrome F, or is another fluorochrome other than F;
L1 is at least one first cleavable linker molecule;
L2 is at least one second cleavable linker molecule; and
B is a linking moiety or a target molecule of interest;
wherein L1 and L2 are different.

A second aspect of the invention relates to a method for the synthesis of a fluorochrome-quencher conjugate of the first aspect. The method includes:
providing a F-L1 molecule;
providing a Q-L2 molecule;
providing a B moiety; and
reacting the mixture to form the conjugate or conjugating the F-L1 molecule and the Q-L2 molecule separately to a biomolecule.

The fluorochrome-quencher conjugate of the first aspect may be used for the detection of a target molecule or biomolecule. Thus, a third aspect of the invention relates to a method of detecting a target molecule, comprising contacting a sample suspected of containing the target molecule with a fluorochrome-quencher conjugate of the first aspect, and measuring the fluorescence. In another aspect, a modified nucleotide comprising a fluorochrome-quencher conjugate of the first aspect is provided. In this case, the moiety B is a nucleotide. The modified nucleotide may be used for DNA sequencing by synthesis.

In yet another aspect, a modified oligonucleotide comprising a fluorochrome-quencher conjugate of the first aspect is provided. In this case, the moiety B is an oligonucleotide. The modified oligonucleotide may be used for sequencing by ligation, sequencing by hybridization, or fluorescence in situ hybridization for detection of DNA or RNA such as mRNA, rRNA, or miRNA.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

Figure 1:
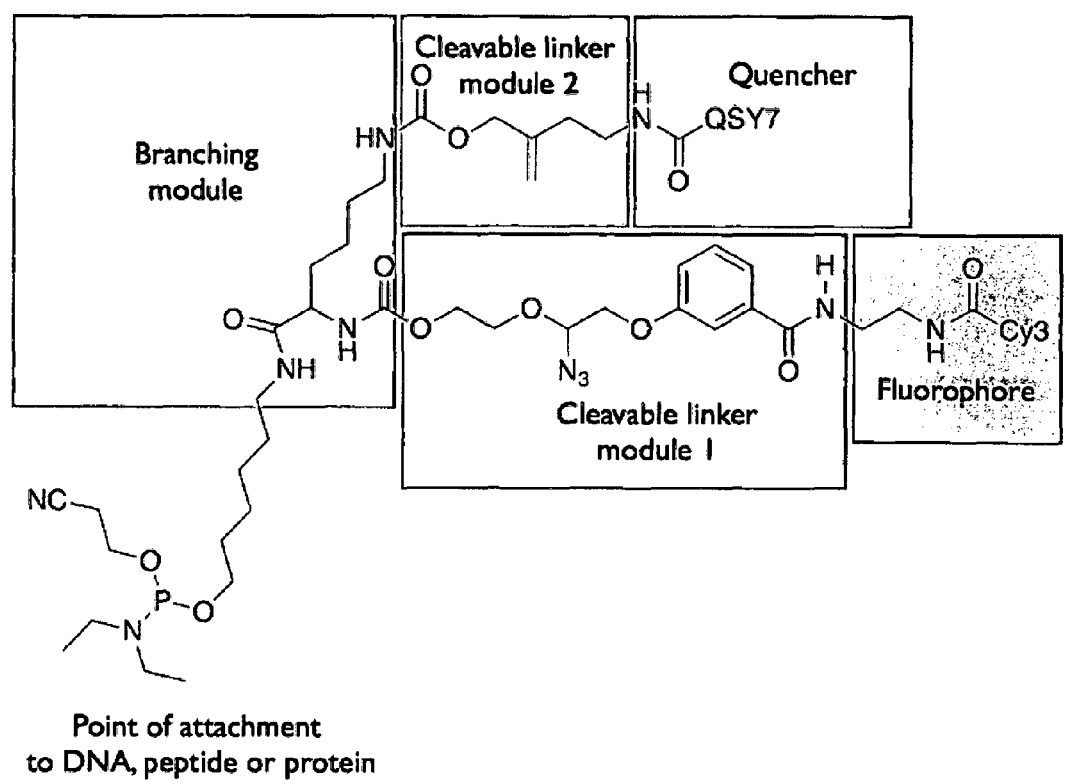
FIG. 1 shows a schematic diagram of present fluoromodule incorporating fluorophore, quencher, cleavable linkers, a branching or linking module to connect the quencher and fluorophore, and a point of attachment to the biomolecule of interest.

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural or chemical changes may be made without departing from the scope of the invention. The various embodiments are not necessarily mutually exclusive, as some embodiments can be combined with one or more other embodiments to form new embodiments.

Aspects of the invention aim to develop orthogonal cleavable chemistries to link quenchers to fluorochromes in order to tune their on-off signals. The fluorescence of fluorochromes may then be revealed using an external chemical stimulus to cleave the linkers and thereby release quenchers. This strategy allows the use of the external chemical reagents to increase the repertoire of available fluorochromes. One application of this strategy lies in DNA sequencing. Only one fluorochrome-quencher pair may be sufficient to detect all four nucleotides in sequencing-by-synthesis, by using four different cleavable linkers. In sequencing-by-ligation or sequencing-by-hybridization, the use of cleavable chemistry can greatly increase the limited number of fluorochrome-linked-probes currently used by other methods.

Present invention encompasses the development of a set of cleavable fluoromodules, which are individually made up of a fluorochrome and a quencher, both conjugated to any biomolecule of interest via orthogonal and mildly cleavable linkers. Currently, several second-generation sequencing techniques use cleavable linkers to conjugate fluorophores to reversible terminator nucleotides, so that the fluorophore can be subsequently released to incorporate the next labelled nucleotide. This demonstrated the feasibility of using cleavable linkers in sequencing techniques. Accordingly, possible applications of presently disclosed cleavable fluorochrome-quencher pairs include labeling of nucleotides for sequencing by synthesis or labeling of oligonucleotides for sequencing by ligation, sequencing by hybridization and other hybridization based applications such as fluorescence in situ hybridization (FISH) for detection of DNA and RNA such as mRNA, rRNA, or miRNA.

In present strategy, quenchers are incorporated or conjugated to fluorochromes, such as fluorophores, through cleavable linkers, so that the fluorescence signal of the fluorophores can be turned on or off by the addition of an external cleavage reagent. By using multiple different cleavable linkers and reagent pairs, this provides an easy and efficient method of differentiating different target molecules.

Thus, in a first aspect of the invention, there is disclosed a fluorochrome-quencher conjugate having the structure

F-L1-B-L2-Q wherein

F is at least one fluorochrome;

Q is at least one quenching molecule for the at least one fluorochrome, or is another fluorochrome F, or is another fluorochrome other than F;

L1 is at least one first cleavable linker molecule;

L2 is at least one second cleavable linker molecule; and

B is a linking moiety or a target molecule of interest;

wherein L1 and L2 are different.

In present context, a fluorochrome can be either a chromophore or a fluorophore. A chromophore is a molecule that has the ability to absorb energy from light and emit colour. The absorption of light excites electrons to higher energy levels but the electron relaxes to the ground state without releasing photons. A fluorophore is a molecule that has the ability to absorb energy from light, transfer this energy internally, and emit this energy (i.e. photon) as light of a characteristic wavelength. Unless otherwise stated, a fluorochrome, in the present context, may generally be seen as a label tag that emits colour upon light irradiation regardless of the mode of fluorescence, and can include a fluorophore or reporter label. For the sake of brevity and illustration, the following discussion refers to a fluorophore and reference to a fluorophore includes reference to a chromophore. However, it is to be understood and appreciated by a person skilled in the art that the scope of the invention is not limited as such. Briefly, following the absorption of energy (a photon) from light, a fluorophore will be raised from its ground state to a higher vibrational level of an excited singlet state. In the next phase, some energy is lost as heat, returning the fluorophore to the lowest vibrational level of an excited singlet state. From this excited singlet state, the fluorophore can return to its ground state, either by emission of light (a photon) or by a non-radiative energy transition. Light emitted from the excited singlet state is called fluorescence. Since some energy is lost during this process, the energy of the emitted fluorescence light is lower than the energy of the absorbed light, and therefore emission occurs at a longer wavelength than absorption. Different processes can decrease the intensity of fluorescence. Such decreases in fluorescence intensity are called "quenching" and can be caused by molecules termed as quenchers or quenching molecules. The quenching molecule may be another fluorophore different from the first fluorophore, or may be a non-fluorescent molecule.

The expression "at least one" can refer to one, two, three, four, or more elements.

The linking moiety B is conjugated at one site to the at least one first cleavable linker molecule L1 and at another site to the at least one second cleavable linker molecule L2. L1 and L2 can be selectively cleaved or cut off from B under suitable conditions, such as by using suitable cleaving agents.

FIG. 1 shows a schematic diagram of the modular system of present fluoromodule containing a fluorophore-quencher pair and cleavable linkers. In present context, the terms "fluoromodule" and "fluorophore-quencher conjugate" are used interchangeably.

As illustrated, the at least one fluorophore F is conjugated to the at least one first cleavable linker molecule L1 at one site of L1, the at least one quenching molecule Q is conjugated to the at least one second cleavable linker molecule L2 at one site of L2. Another site of L1 and another site of L2 are conjugated to different sites of the linking moiety B. A target molecule or biomolecule may be attached to yet a further site of the linking moiety B. In other words, F, Q, B, L1 and L2 may be coupled to each other through conjugation chemistry, such as amide chemistry.

The present fluorophore-quencher conjugate can be said to be modular since the conjugate comprises the respective 'modules' F, Q, L1, L2, and B. In the illustration shown in FIG. 1, the respective module is clearly shown in the respective individual box.

Figure 3:
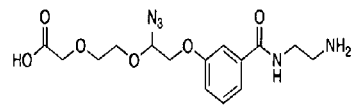
FIG. 3 lists some examples of cleavable linkers and cleavage reagents to be used for the present fluoromodule. Each linker has been designed to include an amine functionality and a carboxylic acid or hydroxyl functionality so that it can be compatible with amide synthesis conditions in peptide synthesis.
Figure 3:
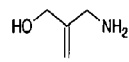
Figure 3:
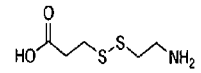
Figure 3:
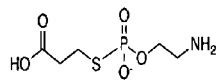
Figure 3:
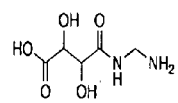
Figure 3:
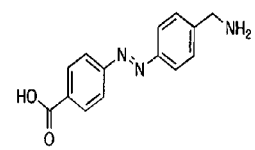
Figure 3:
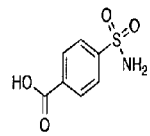
Figure 3:
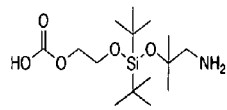

Staudinger ligation with azides, Pd-catalyzed deallylation, reductive cleavage of diazobenzenes, disulfides, phosphorothioates, acylsulfonamides and periodate cleavage of diols are examples of reactions that can serve as cleavable linkers (FIG. 3). Cleavage conditions are developed so that the cleavage reactions can be accomplished within minutes, at a near quantitative yield. The cleavable reactions listed above have been selected for close to quantitative yield in other conditions. In case of less than quantitative yield in the conditions of the experiment, it could still be possible to develop methods to deconvolute fluorescence data for accurate interpretation.

Accordingly, in various embodiments, the at least one first cleavable linker L1 may be selected from cleavable linkers such as azido linker, allyl linker, disulfide linker, phosphorothioate linker, diol linker, diazobenzene linker, acylsulfonamide linker, and silyl linker.

Similarly, in various embodiments; the at least one second cleavable linker L2 may be selected from cleavable linkers such as azido linker, allyl linker, disulfide linker, phosphorothioate linker, diol linker, diazobenzene linker, acylsulfonamide linker, and silyl linker.

In certain embodiments, the at least one first cleavable linker L1 and the at least one second cleavable linker L2 may be independently selected from the group consisting of:

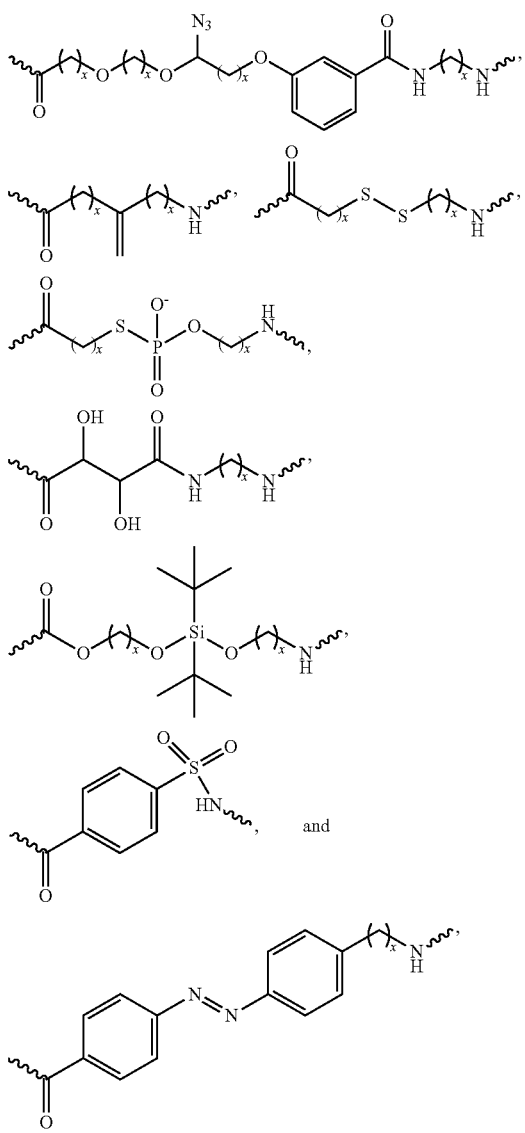

wherein x is independently selected and is an integer of between 1 and 10. As mentioned above, L1 and L2 are selected to be different from each other.

To conjugate the cleavable fluoromodule to biomolecules, they can be derivatized to the phosphoramidites, and incorporated directly to oligonucleotides during automated chemical synthesis. A postsynthetic incorporation of the fluoromodule can also be developed, where the point of attachment is derivatized to the succinimidyl ester for conjugation to a 5'-amine-functionalized oligonucleotide, or amine functionalities of peptide or protein.

A modular approach towards the design of the cleavable fluoromodule has been taken. As shown in FIG. 3, each component of the fluoromodule is put together using amide coupling. This allows to harness the activation and coupling strategies that have been developed for peptide synthesis. Cleavable linkers can be derivatized with the same functional groups for coupling, and each module can be interchanged, with the convenience of the same coupling chemistries.

According to various embodiments, the at least one fluorophore F may be selected from the group consisting of Cy3, Cy5, FAM, TET, HEX, TMR, ROX, Texas red, LC red 640, and LC red 70. In certain embodiments, F may be Cy3.

In various embodiments, the at least one quenching molecule Q may be selected from the group consisting of QSY-7, DDQ-I, Dabcyl, Eclipse, Iowa Black FQ, BHQ-1, BHQ-2, DDQ-II, Iowa Black RQ, QSY-21, and BHQ-3. In certain embodiments, Q may be QSY-7. In a further embodiment, F may be Cy3 and Q may be QSY-7.

In cases where Q is another fluorophore other than F, Q undergoes Forster resonance energy transfer (FRET) with F such that a fluorescence emission wavelength change occurs upon removal of Q. For example, the another fluorophore other than F may be Cy3 and Q may be Cy5.

In various embodiments, L1-F and L2-Q may be separately conjugated to a respective biomolecule and are spaced at a distance apart for quenching of the fluorescence or FRET to occur.

The biomolecule may be selected from the group consisting of nucleic acids, lipids, peptides and proteins.

In various embodiments, B may be a linking moiety and further include a reactive group R for coupling the conjugate to a target molecule. The target molecule may be an amino acid, a peptide, a polypeptide, a nucleotide, an oligonucleotide, or a polynucleotide. In other embodiments, B may be the target molecule, such as an oligonucleotide (see examples below).

In certain embodiments, B has the structure:

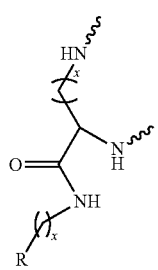

wherein R is selected from the group consisting of hydroxyl, carboxyl, and amine.

In certain embodiments, the conjugate may be one of the following:

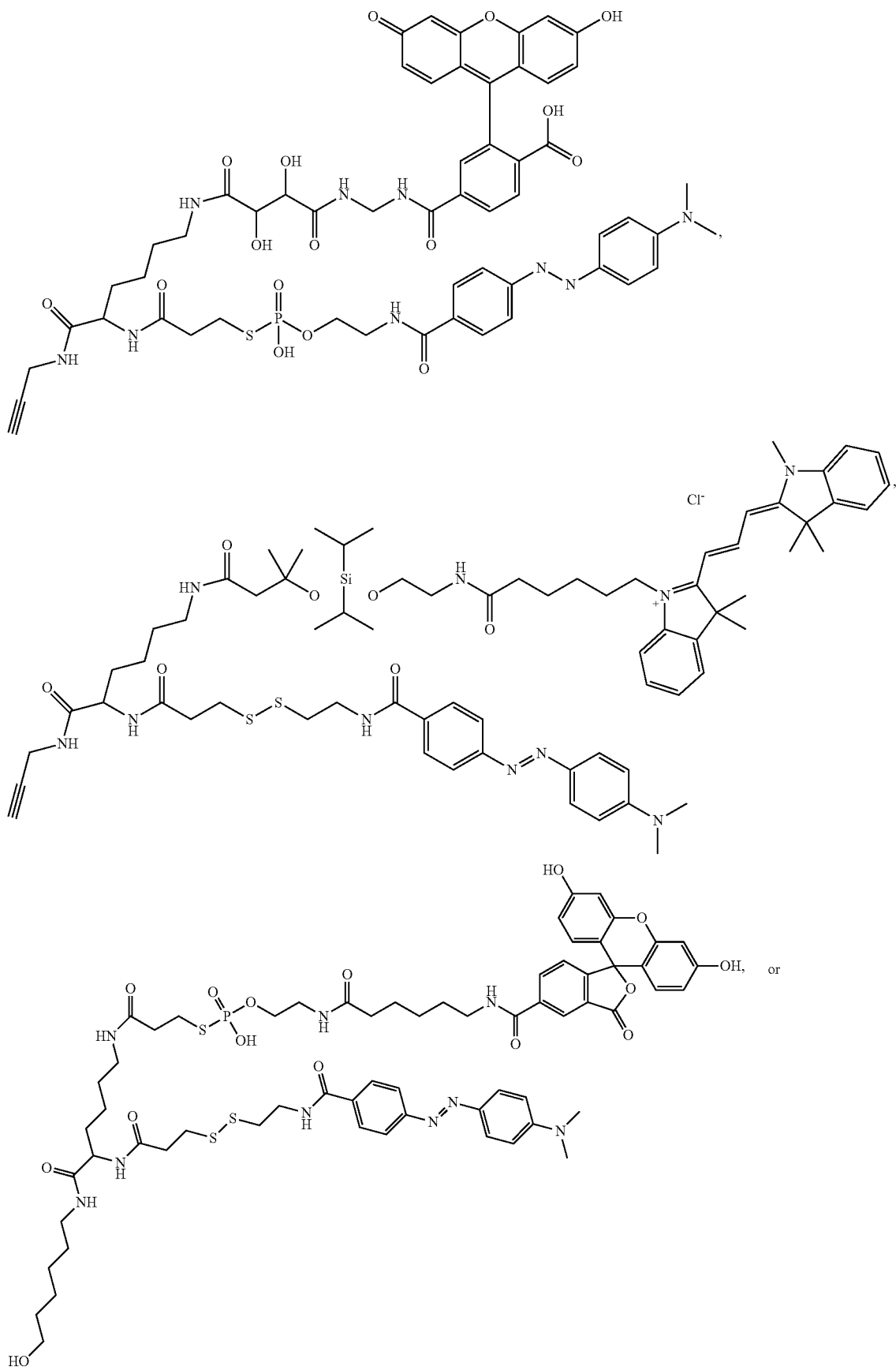

-continued

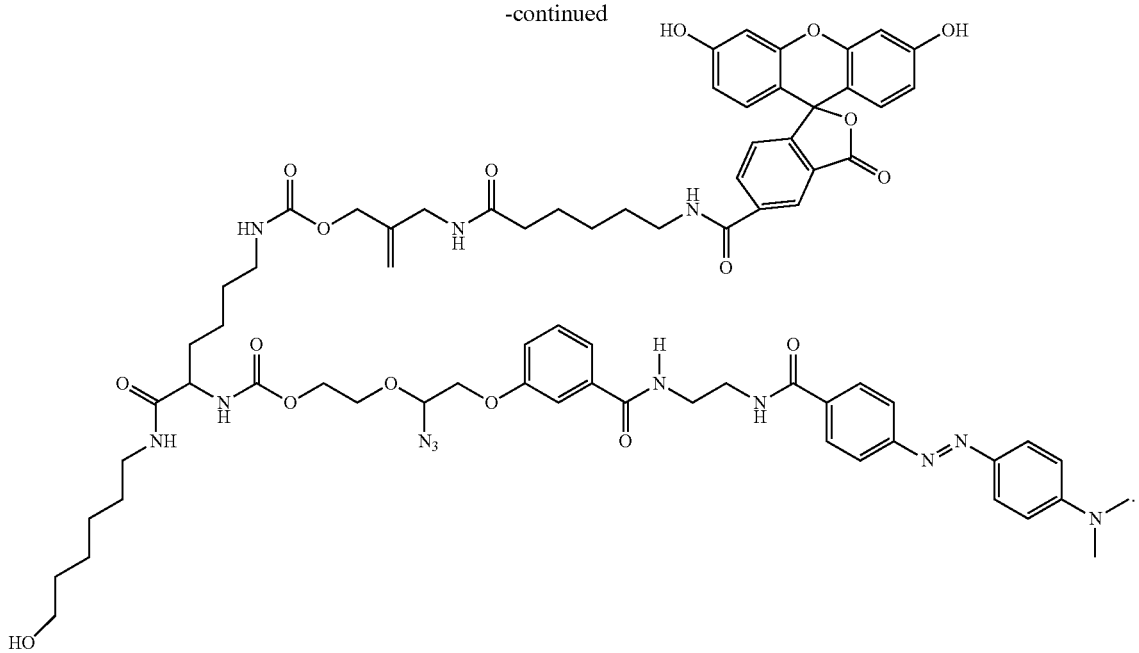

To synthesize the present fluorophore-quencher conjugate, a mixture of a F-L1 molecule, a Q-L2 molecule, and a B moiety may be reacted to form the conjugate or the F-L1 molecule and the Q-L2 molecule may be conjugated separately to a biomolecule.

To detect a target molecule, a sample suspected of containing the target molecule may be contacted with a fluorophore-quencher conjugate presently disclosed and measuring the fluorescence. Prior to measuring the fluorescence, the at least one first and/or the at least one second linker molecule may be selectively cleaved, wherein cleavage is achieved by adding at least one selective cleavage reagent or incubating the sample under conditions that allow selective cleavage of the at least one first or the at least one second linker molecule.

Figure 2:
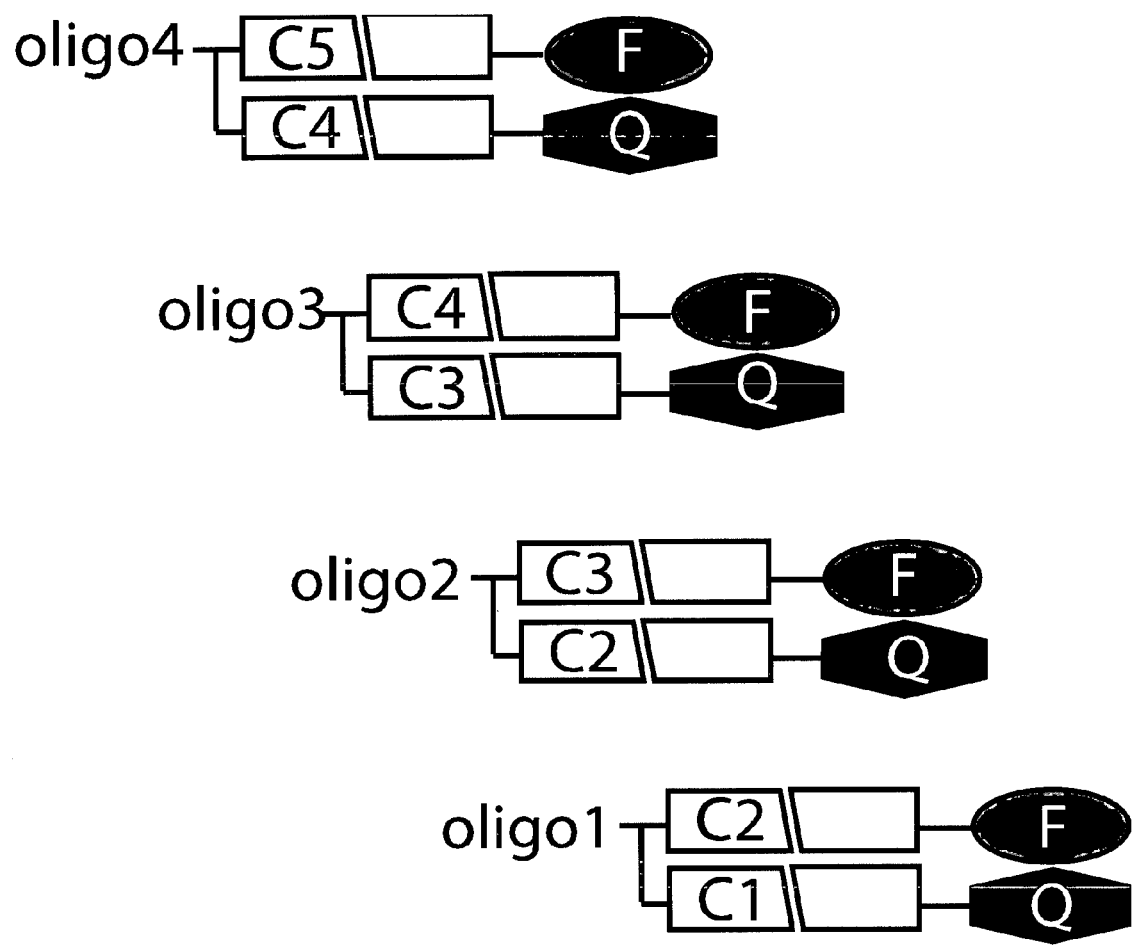
FIG. 2 shows a schematic representation of the use of one fluorophore-quencher coupled with 5 cleavable chemistries for detecting 4 different targets. This expands the capability of currently available fluorophores by introducing an additional dimension of control to the fluorophores by conferring external control using a chemical stimuli reagent.

Present invention is particularly useful in multiplex detection of targets. By conferring an additional dimension of control to the fluorophores through an external chemical stimulus, fluorescence can be controlled and more targets can be detected with just one fluorophore-quencher pair. For instance, one fluorophores-quencher pair matched with 5 different linkers will allow detection of 4 different targets (FIG. 2). This saves on the number of individual lasers required for different fluorophores. A combination of 4 different fluorophores, and 5 different cleavable chemistries will allow a detection of (4×4) 16 different targets. This allows for multiplexing that is currently not observed in fluorescence applications such as sequencing.

Accordingly, a method of detecting two or more targets of interest is herein disclosed. The method includes:
  contacting a sample suspected of containing the two or more targets of interest with two or more fluorophore-quencher conjugates presently disclosed, wherein F and Q of each of the two or more fluorophore-quencher conjugate are the same, wherein L1 and L2 of each of the two or more fluorophore-quencher conjugate are different; and
  measuring the fluorescence.

In various embodiments, the method may further include selectively cleaving the at least one first and/or the at least one second linker molecule in each of the two or more fluorophore-quencher conjugate prior to measuring the fluorescence, wherein cleavage is achieved by adding at least one selective cleavage reagent or incubating the sample under conditions that allow selective cleavage of the at least one first or the at least one second linker molecule of each of the two or more fluorophore-quencher conjugate.

In various embodiments where B is a nucleotide, i.e. a modified nucleotide comprising the fluorochrome-quencher conjugate defined above, the modified nucleotide may be used for DNA sequencing by synthesis.

In various embodiments where B is an oligonucleotide, i.e. a modified oligonucleotide comprising the fluorochrome-quencher conjugate defined above, the modified oligonucleotide may be used for sequencing by ligation, sequencing by hybridization, or fluorescence in situ hybridization for detection of DNA or RNA.

In order that the invention may be readily understood and put into practical effect, particular embodiments will now be described by way of the following non-limiting examples.

Examples

Phosphothioate Linker

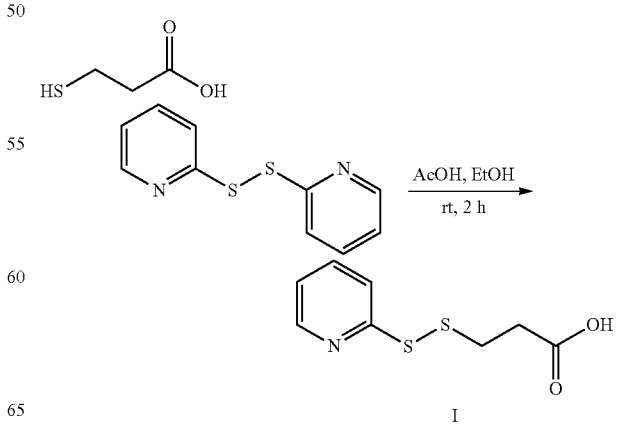

I

Dipyridyldisulfide (5.00 g, 22.7 mol) was dissolved in 35 mL of anhydrous Ethanol. Acetic acid (0.7 mL) and 3-mercaptopropionic acid (1.20 g, 11.3 mmol) were added. The reaction mixture was stirred at room temperature for 2 h.

reaction was filtered and yellow solid was obtained as residue (0.4217 g, 92%). $^1$H NMR (400 MHz, DMSO-d6) δ 2.53-2.61 (m, 2H), 2.66 (dd, J=13.4, 6.6 Hz, 2H), 3.48 (d, J=4.8 Hz, 2H), 3.85 (dt, J=10.5, 5.0 Hz, 2H).

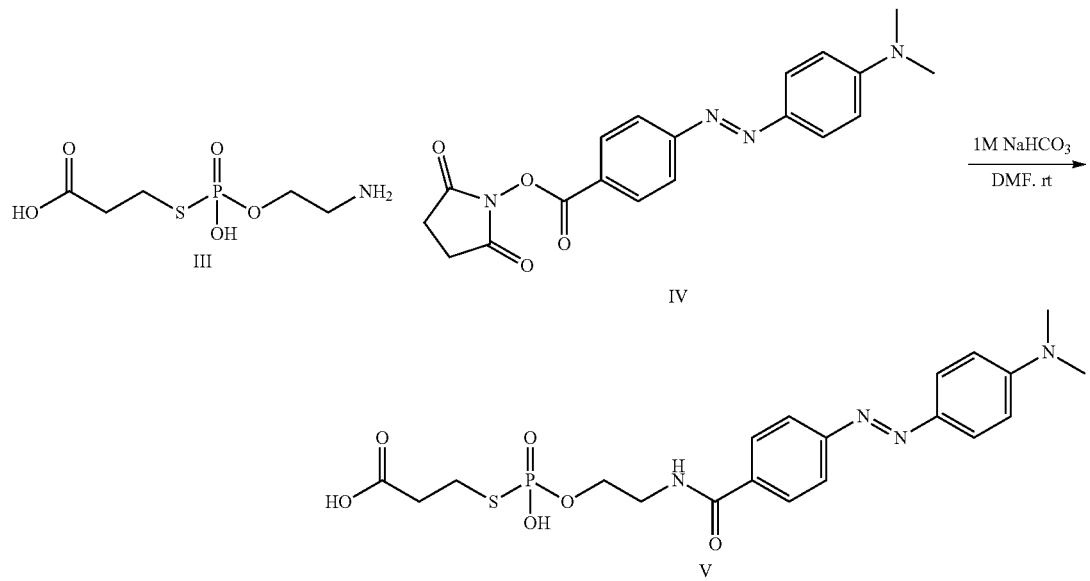

Solvent was removed in vacuo. Yellow oil was obtained and put under high vacuum to remove traces of acetic acid. Residue was purified with neutral alumina column with 3:2 dichloromethane:ethanol as the eluent. 4% acetic acid was added to the eluent after the yellow band by-product had eluted. Viscous light yellow oil was obtained and placed under high vacuum to remove acetic acid. Yellow-white crystals was obtained (1.70 g, 70%). $^1$H NMR (400 MHz, CDCl$_3$) δ 2.80 (t, 2H, 6.9 Hz), δ 3.05 (t, 2H, 6.9 Hz), δ 7.14 (m, 1H), δ 7.66 (m, 2H), 8.48 (d, 1H, 6.1 Hz). $^{13}$C NMR (101 MHz, CDCl$_3$): δ 33.9, 34.2, 120.6, 121.3, 137.5, 149.6, 159.5, 176.5.

Compound III (0.08 g, 0.35 mmol) was dissolved in distilled water (10 mL). Compound IV (0.128 g, 0.35 mmol) was dissolved in dimethylformamide (70 mL) and added to Compound III. 1M NaHCO$_3$ (8 mL) was added into the mixture. Reaction was stirred overnight. Solvents were removed in vacuo. Residue was purified with column chromatography. m/z—481 (MH$^+$).

Diol Linker

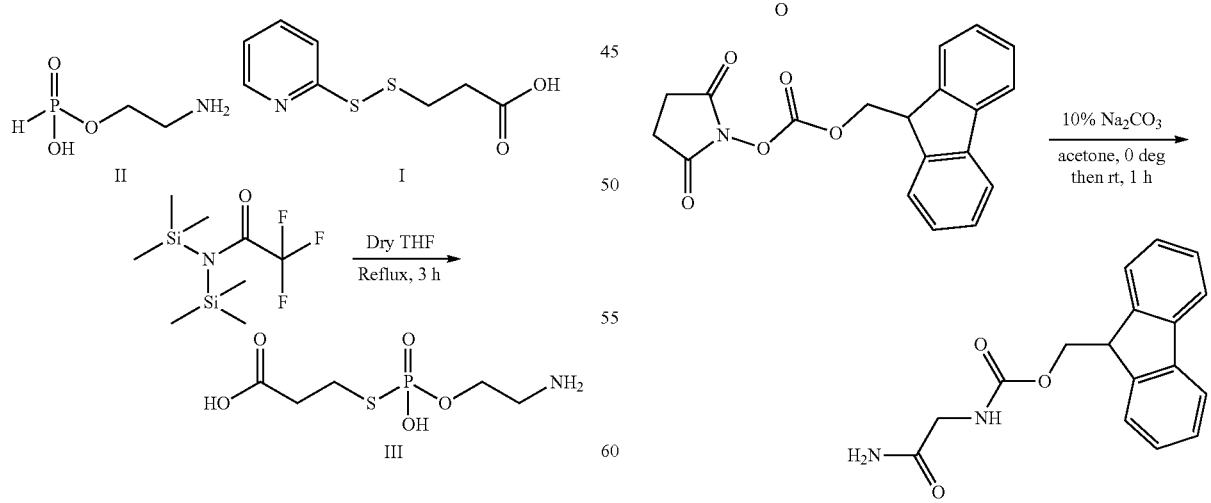

Compound I (0.65 g, 3.0 mmol) was dissolved in dry THF (10 mL). Compound II (0.25 g, 2.0 mmol) and N,O-Bis(trimethylsilyl)trifluoroacetamide (1.59 mL, 6.0 mmol) were dissolved in dry THF (30 mL). This mixture was added to Compound I. Reaction was stirred under reflux for 3 h. The Glycinamide hydrochloride (3.28 g, 0.03 mol) was dissolved in acetone (83 mL) and 10% Na$_2$CO$_3$ (200 mL) and mixture was cooled to 0° C. Fmoc-OSu (10.0 g, 0.03 mol)

was dissolved in acetone (83 mL) and was added dropwise over 30 minutes to the reaction mixture. After addition, reaction mixture was stirred for 1 hour at room temperature. The reaction mixture was concentrated in vacuo and the residue was dissolved in AcOEt. The solution was washed with 2N citric acid, saturated NaHCO₃, brine and dried over Na₂SO₄. After filtration, filtrate was evaporated in vacuo and recrystallised from MeOH to give Compound VI (6.43 g, 72%). ¹H NMR (400 MHz, CDCl₃) δ 3.82 (d, J=4.7 Hz, 2H), 4.20 (t, J=6.6 Hz, 1H), 4.45 (d, J=6.6 Hz, 2H), 7.30 (td, J=7.5, 1.2 Hz, 2H), 7.38 (t, 2H, J=7.5 Hz), 7.58 (d, J=7.4 Hz, 2H), 7.75 (d, J=7.5 Hz, 2H). MS m/z 297 (MH⁺).

the residue was dissolved in AcOEt. The organic layer was washed with 2N citric acid, brine and dried over Na2SO4. After filtration, the filtrate was evaporated in vacuo as crude (Compound VIII). ¹H NMR (400 MHz, Acetone-d6) δ 1.19 (t, J=7.1 Hz, 1H), 1.95 (d, J=7.0 Hz, 1H), 2.05 (dq, J=4.4, 2.2 Hz, 7H), 2.77-2.97 (m, 4H), 3.07-3.19 (m, 6H), 4.18-4.27 (m, 3H), 4.30-4.36 (m, 2H), 4.42 (d, J=1.9 Hz, 1H), 4.54-4.71 (m, 3H), 7.31 (t, J=7.4 Hz, 3H), 7.40 (t, J=7.3 Hz, 2H), 7.69 (d, J=7.5 Hz, 2H), 7.84 (d, J=7.5 Hz, 2H). MS m/z 401.1 (MH⁺).

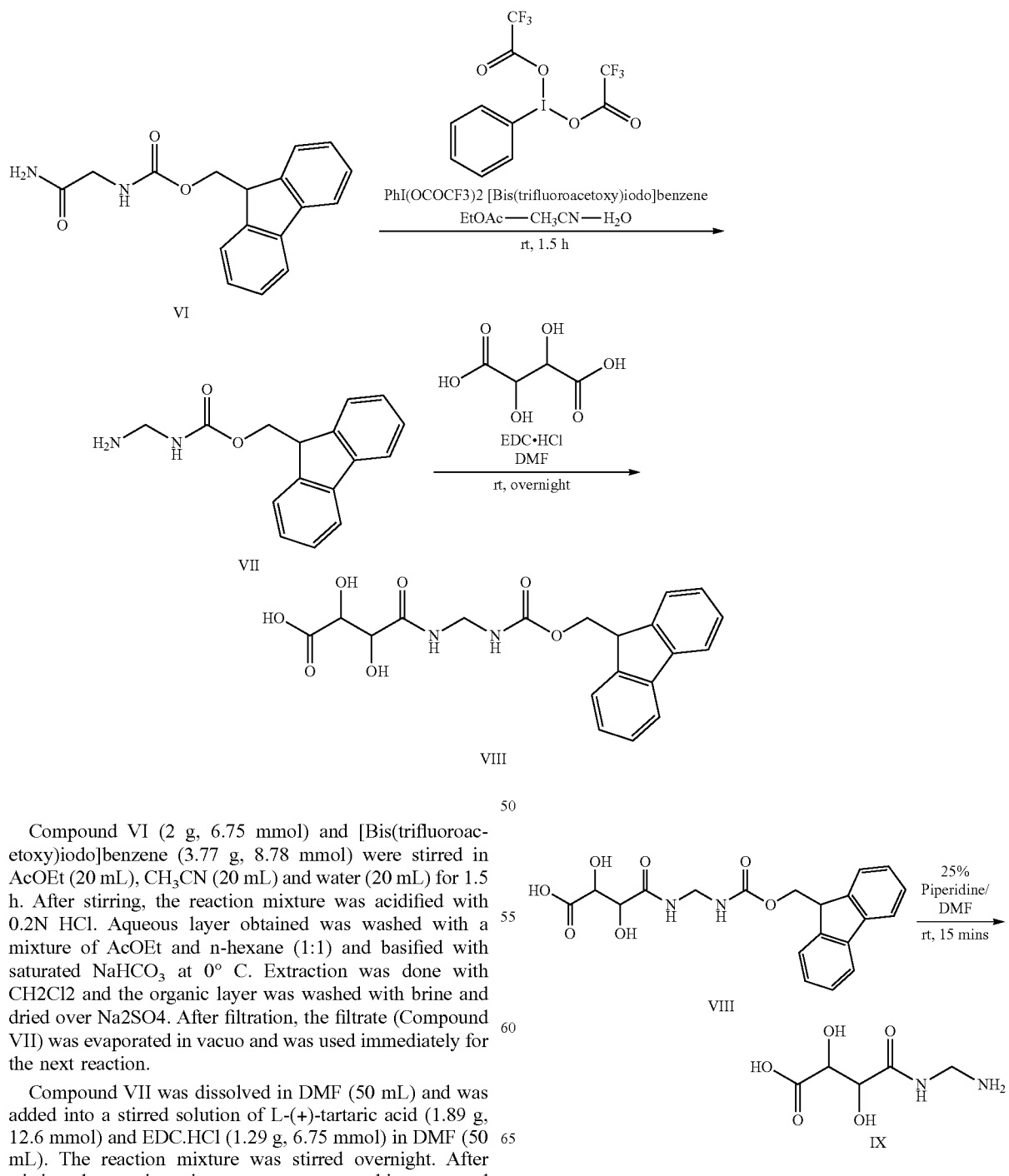

Compound VI (2 g, 6.75 mmol) and [Bis(trifluoroacetoxy)iodo]benzene (3.77 g, 8.78 mmol) were stirred in AcOEt (20 mL), CH₃CN (20 mL) and water (20 mL) for 1.5 h. After stirring, the reaction mixture was acidified with 0.2N HCl. Aqueous layer obtained was washed with a mixture of AcOEt and n-hexane (1:1) and basified with saturated NaHCO₃ at 0° C. Extraction was done with CH2Cl2 and the organic layer was washed with brine and dried over Na2SO4. After filtration, the filtrate (Compound VII) was evaporated in vacuo and was used immediately for the next reaction.

Compound VII was dissolved in DMF (50 mL) and was added into a stirred solution of L-(+)-tartaric acid (1.89 g, 12.6 mmol) and EDC.HCl (1.29 g, 6.75 mmol) in DMF (50 mL). The reaction mixture was stirred overnight. After stirring, the reaction mixture was concentrated in vacuo and Compound VIII was stirred in DMF (15 mL) and piperidine (5 mL) for 15 mins. Solvents were removed in vacuo. Solid was dissolved in MeOH and insoluble particles were filtered off. Filtrate was dry-loaded and purified using flash chromatography (30% MeOH/DCM—100% MeOH) to give Compound IX as yellowish-white solid (300 mg, 25%).

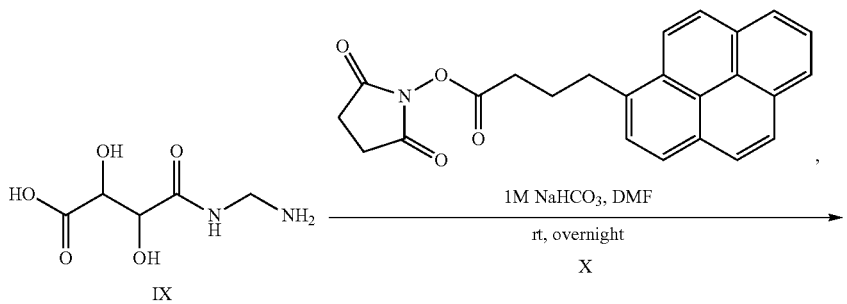

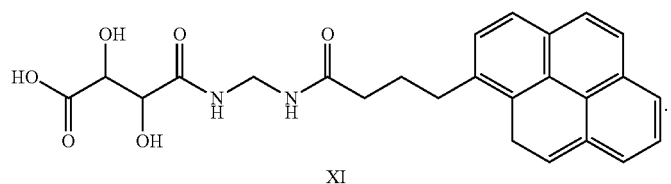

Compound IX (150 mg, 0.842 mmol) was dissolved in water (15 mL) and was added to Pyrene-NHS (Compound X) (324 mg, 0.842 mmol) in DMF (40 mL). 1M NaHCO3 (6 mL) was added in and the reaction mixture was stirred overnight. Solvents were evaporated in vacuo and residue was dissolved in DCM and MeOH. Insoluble solid was filtered off and washed repeatedly with DCM and MeOH. Filtrate was dry-loaded and purified using flash chromatography to give Compound XI. $^1$H NMR (400 MHz, DMSO-d6) δ 1.95-2.05 (m, 2H), 2.67 (p, J=1.8 Hz, 3H), 3.55-3.61 (m, 2H), 4.37-4.53 (m, 2H), 4.83 (d, J=2.0 Hz, 1H), 4.88 (t, J=2.2 Hz, 1H), 7.94 (d, J=7.8 Hz, 1H), 8.03-8.14 (m, 3H), 8.20-8.31 (m, 4H), 8.39 (d, J=9.3 Hz, 1H). MS m/z 447.15 (M−H)$^-$.

Silyl Linker

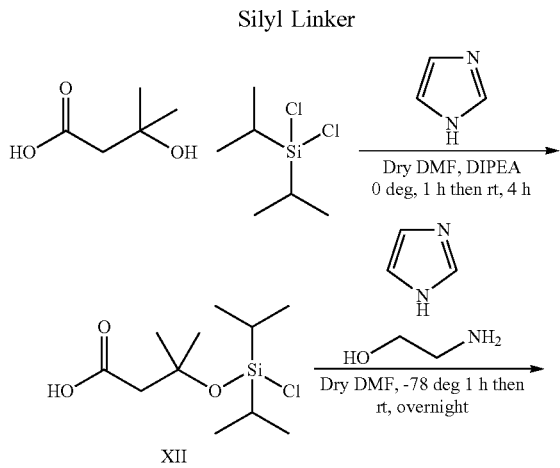

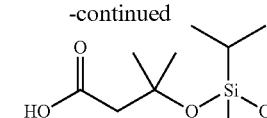

3-hydroxy-3-methylbutyric acid (1 g, 8.46 mmol) and imidazole (0.69 g, 10.1 mmol) was dissolved in DMF (16 mL). DIPEA (8.7 mL) was added and the reaction mixture was cooled to 0° C. After cooling, diisopropyldichlorosilane (2.82 g, 15.3 mmol) was added and stirred for 1 h at 0° C., then 4 h at room temperature.

After stirring, the reaction mixture was cooled to −78° C. 2-aminoethanol (1.22 g, 20 mmol) and imidazole (1.37 g, 20 mmol) were dissolved in DMF (16 mL) and added into the reaction mixture. The reaction mixture was stirred for 1 h at −78° C. and then overnight at room temperature. Solvents were removed in vacuo and residue was dissolved in cooled EA (200 mL) and 5% NaHCO$_3$ (200 mL). Organic layer was washed with brine and dried over Na$_2$SO$_4$. After filtration, filtrate was concentrated in vacuo and purified using flash chromatography to obtain a yellow oil (1.5 g, 61%). $^1$H NMR (400 MHz, CDCl3) δ 1.23 (d, J=5.1 Hz, 12H), 1.46 (s, 6H), 2.57 (s, 2H), 3.21-3.27 (m, 2H), 3.62 (d, J=4.8 Hz, 2H), 4.19 (t, J=5.8 Hz, 2H). MS m/z 314.17 (M+Na)$^+$.

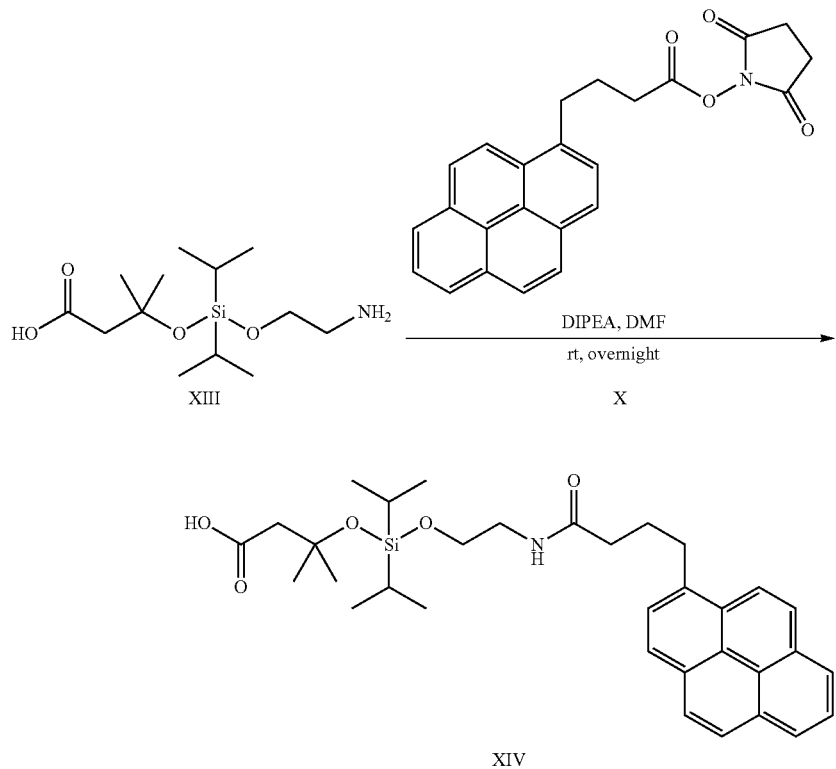

Compound XIII (150 mg, 0.515 mmol) and Pyrene-NHS (Compound X) (132 mg, 0.515 mmol) were dissolved in DMF (30 mL). DIPEA (0.22 mL) was added to the reaction mixture and stirred overnight. Solvents were removed in vacuo and residue was purified using flash chromatography to obtain a yellow solid (0.11 g, 37%). $^1$H NMR (400 MHz, CDCl3) δ 0.94 (d, J=5.7 Hz, 12H), 1.56 (s, 6H), 2.11-2.29 (m, 6H), 3.29-3.38 (m, 6H), 3.74 (t, J=5.4 Hz, 2H), 7.80 (d, J=7.8 Hz, 1H), 7.94-7.99 (m, 4H), 8.13 (dd, J=8.6, 1.3 Hz, 3H), 8.25 (d, J=9.3 Hz, 1H).

Disulfide Linker

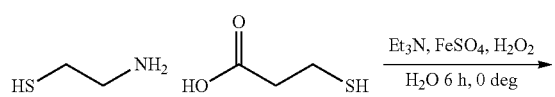

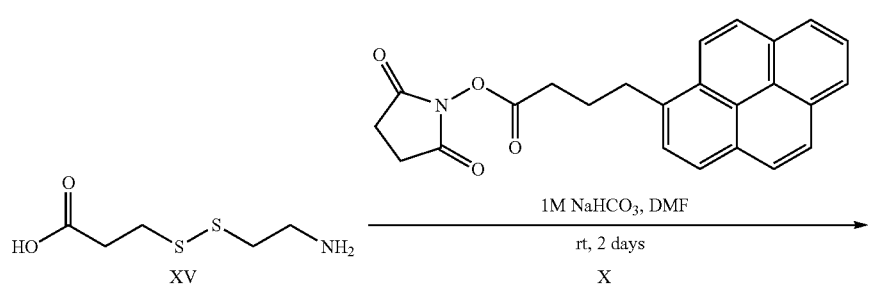

Cysteamine and mercaptopropionic acid were dissolved in water (40 mL) and cooled to 0° C. Triethylamine (8.4 mL, 60 mmol) was added in to the reaction mixture. One crystal of FeSO$_4$ and 16% H$_2$O$_2$ (7 mL) were added dropwise into the reaction mixture. pH was then adjusted to pH 2 with conc. HCl and stirred for 30 mins at room temperature. After stirring, reaction mixture was filtered and washed with cold 0.01N HCl. The filtrate was extracted with EtOAc (40 mL). The aqueous phase was concentrated to 50 mL and purified on a column of Amberlite IRC-50S ion-exchange resin (25 g). Water (pH 5.5) was used to elute out the product (4.5 g, 62%). $^1$H NMR (400 MHz, Deuterium Oxide) δ 2.87 (t, J=6.8 Hz, 2H), 3.05-3.10 (m, 4H), 3.45 (t, J=7.3 Hz, 2H).

-continued

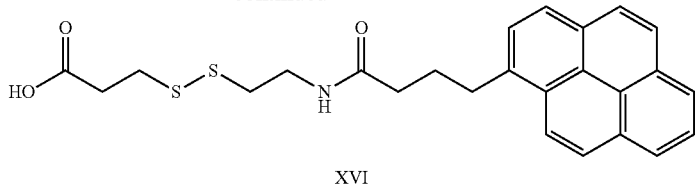

XVI

Compound XV (20 mg, 0.11 mmol) was dissolved in 1M NaHCO3 (1 mL) and was added to Pyrene-NHS (Compound X) (50 mg, 0.13 mmol) dissolved in DMF (25 mL). The reaction mixture was stirred for 2 h at room temperature. Solvents were removed in vacuo and purified using flash chromatography with 5% MeOH/DCM to obtain the product (16 mg, 32%). $^1$H NMR (400 MHz, Methanol-d4) δ 2.15 (m, 2H), 2.36 (dt, J=10.1, 7.1 Hz, 4H), 2.61 (d, J=7.0 Hz, 2H), 2.81 (t, J=6.7 Hz, 2H), 2.90 (t, J=7.0 Hz, 2H), 3.48 (t, J=6.7 Hz, 2H), 7.88 (d, J=7.8 Hz, 1H), 7.94-8.04 (m, 3H), 8.09-8.19 (m, 4H).

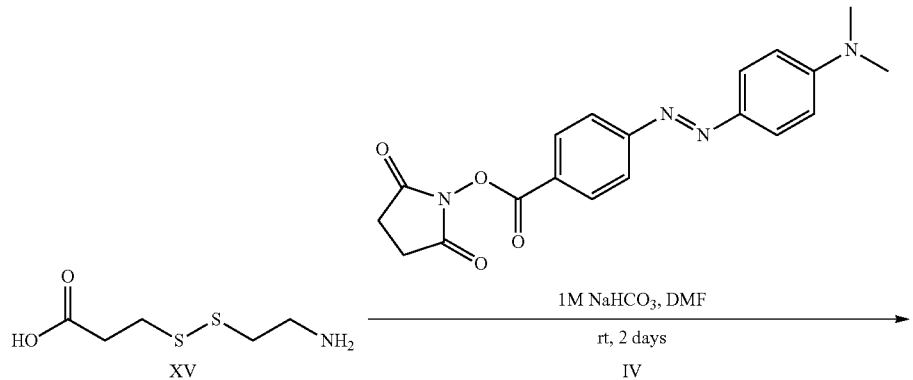

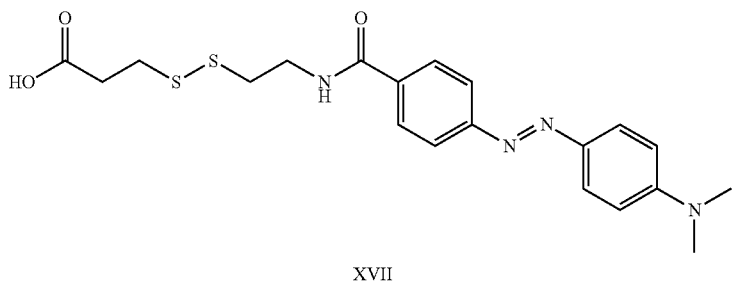

XVII

Compound XV (0.1 g, 0.55 mmol) was dissolved in 0.1M NaHCO3 (6 mL) and was added to Dabcyl-NHS (Compound IV) (0.2 g, 0.55 mmol) dissolved in DMF (25 mL). The reaction mixture was stirred for 2 h at room temperature. Solvents were removed in vacuo and purified using flash chromatography with to obtain the product (60 mg, 25%). NMR (400 MHz, Methanol-d4) δ 2.72 (t, J=7.1 Hz, 2H), 2.98 (td, J=7.0, 3.6 Hz, 4H), 3.11 (s, 6H), 3.72 (t, J=6.9 Hz, 2H), 6.84 (d, J=9.3 Hz, 2H), 7.82-7.88 (m, 4H), 7.92-7.96 (m, 2H). MS m/z 455.12 (M+Na$^+$).

Dabcyl-NHS

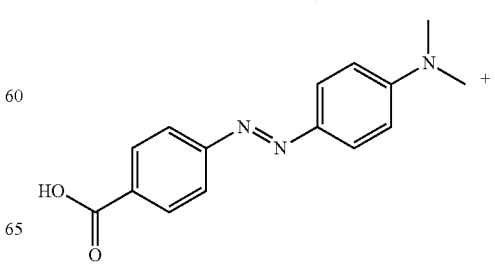

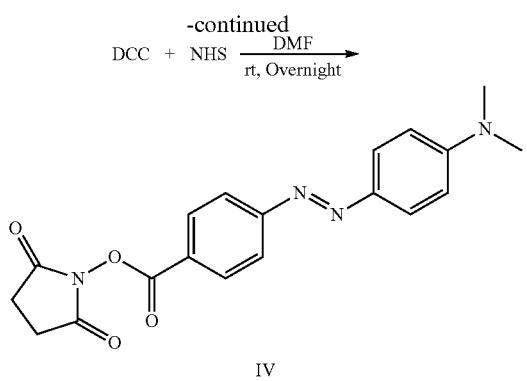

IV p-methyl red (2 g, 7.43 mmol) and N-hydroxysuccinimide (1.11 g, 9.65 mmol) were dissolved in DMF (100 mL) and cooled to 0° C. Dicyclohexylcarbodiimide (1.84 g, 8.91 mmol) was added and stirred for 30 min at 0° C. and then overnight at room temperature. The reaction mixture was filtered and the filtrate was evaporated in vacuo. Residue was precipitated with ether (50 mL), filtered and washed with isopropanol. Orange product (2.3 g, 85%) was obtained. $^1$H NMR (400 MHz, CDCl$_3$) δ 2.92 (s, 4H), 3.12 (s, 6H), 6.76 (d, J=9.2 Hz, 2H), 7.92 (d, J=8.9 Hz, 4H), 8.23 (d, J=8.6 Hz, 2H). m/z—367.34 (MH)$^+$.

Pyrene-NHS

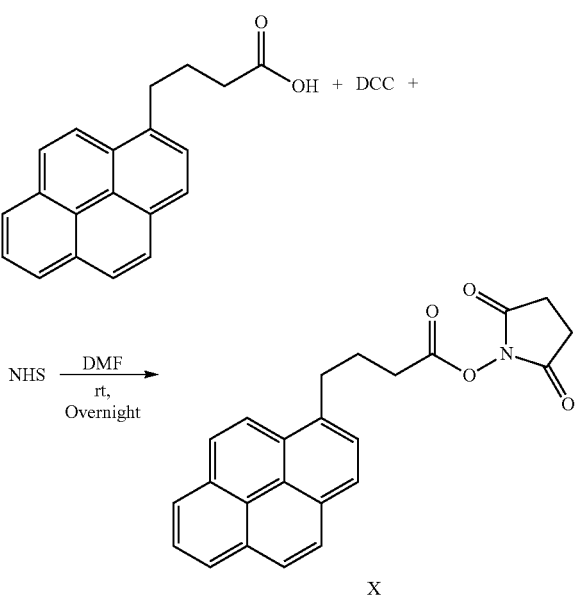

X 1-pyrenebutyric acid (2 g, 6.94 mmol) and N-hydroxysuccinimide (0.96 g, 8.32 mmol) were dissolved in DMF (20 mL). Solution was cooled to 0° C. and 1,3-dicyclohexylcarbodiimide (1.43 g, 6.94 mmol) was added. The reaction mixture was stirred overnight at room temperature. Reaction mixture was filtered and filtrate was evaporated in vacuo. Yellow solid obtained after evaporation was purified by recrystallization from ethanol to obtain the product (2.19 g, 82%). $^1$H NMR (400 MHz, CDCl$_3$) δ 2.27-2.37 (m, 2H), 2.74 (t, J=7.1 Hz, 2H), 2.87 (s, 4H), 3.46-3.53 (m, 2H), 7.90 (d, J=7.8 Hz, 1H), 7.97-8.06 (m, 3H), 8.10-8.20 (m, 5H), 8.30 (d, J=9.3 Hz, 1H). m/z—408.12 (M+Na)$^+$.

Figure 4:
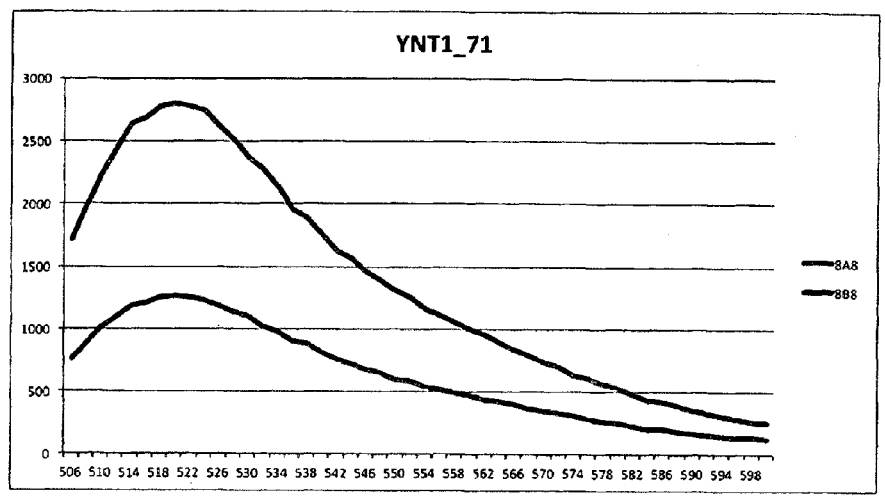
FIG. 4 shows an example of a fluoromodule with a phosphorothioate linked fluorescein and disulfide linked dabcyl was synthesized. Upon the cleavage of the disulfide linked quencher dabcyl, the fluorescence intensity of fluorescein was enhanced.
Figure 4:
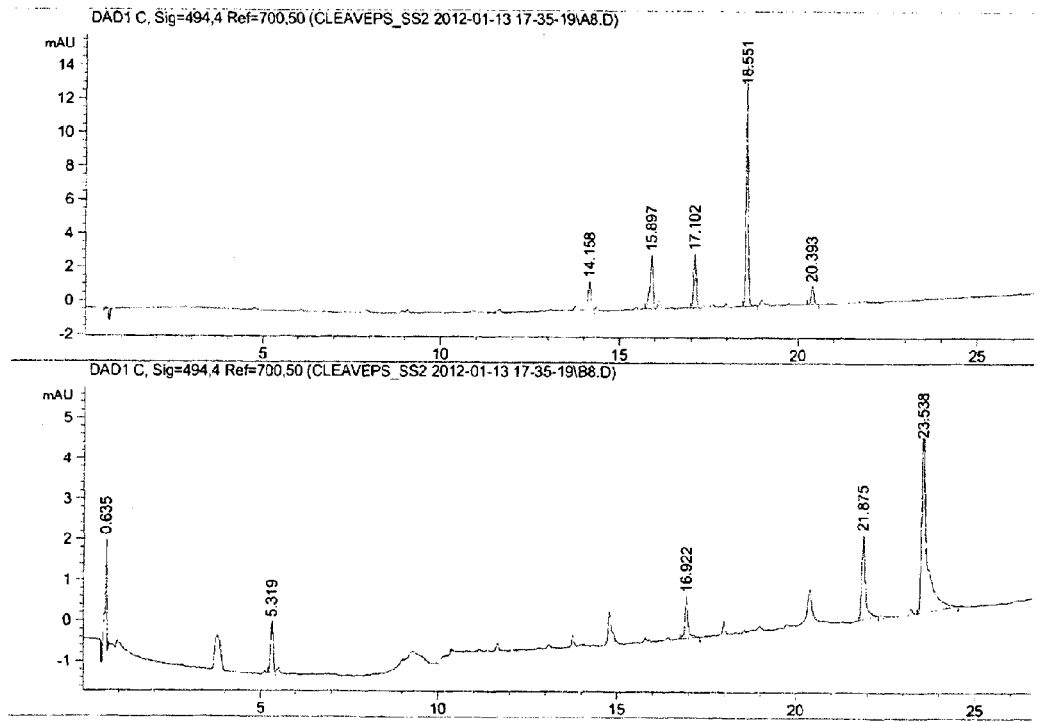
Figure 5:
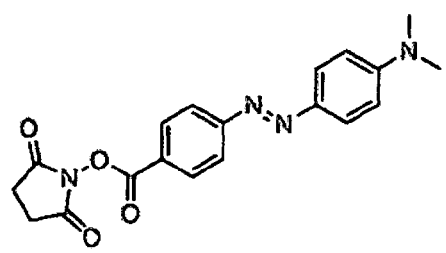
FIG. 5 shows few examples of the chemical structures of fluorophores and quencher.

An example of the enhancement of fluorescence intensity upon cleavage of the linker conjugated to a quencher, dabcyl is shown in FIG. 4. When the disulfide linked quencher is cleaved, the fluorescence of the remaining phosphorothioate-linked fluorophore, fluorescein in this case, increased.

Targets with Cleavable Linkers Attached to an Alkyne-Branched Moiety

Synthesis of Alkyne-Functionalized Branch

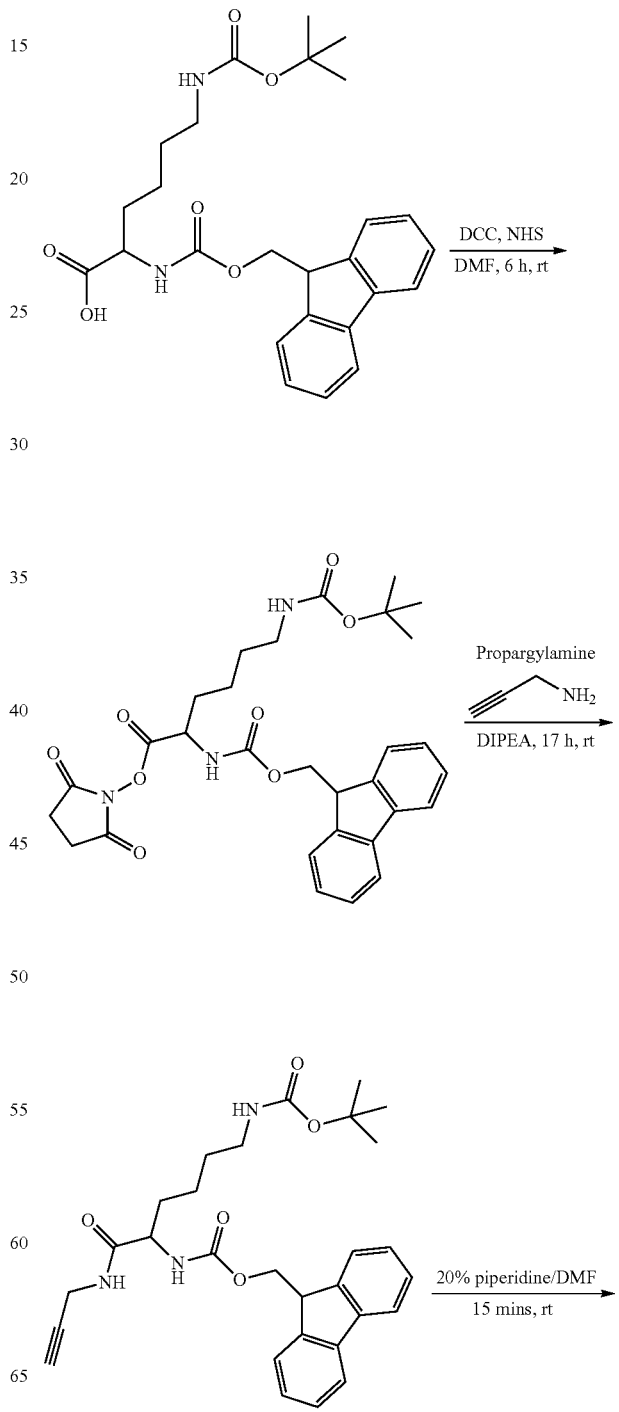

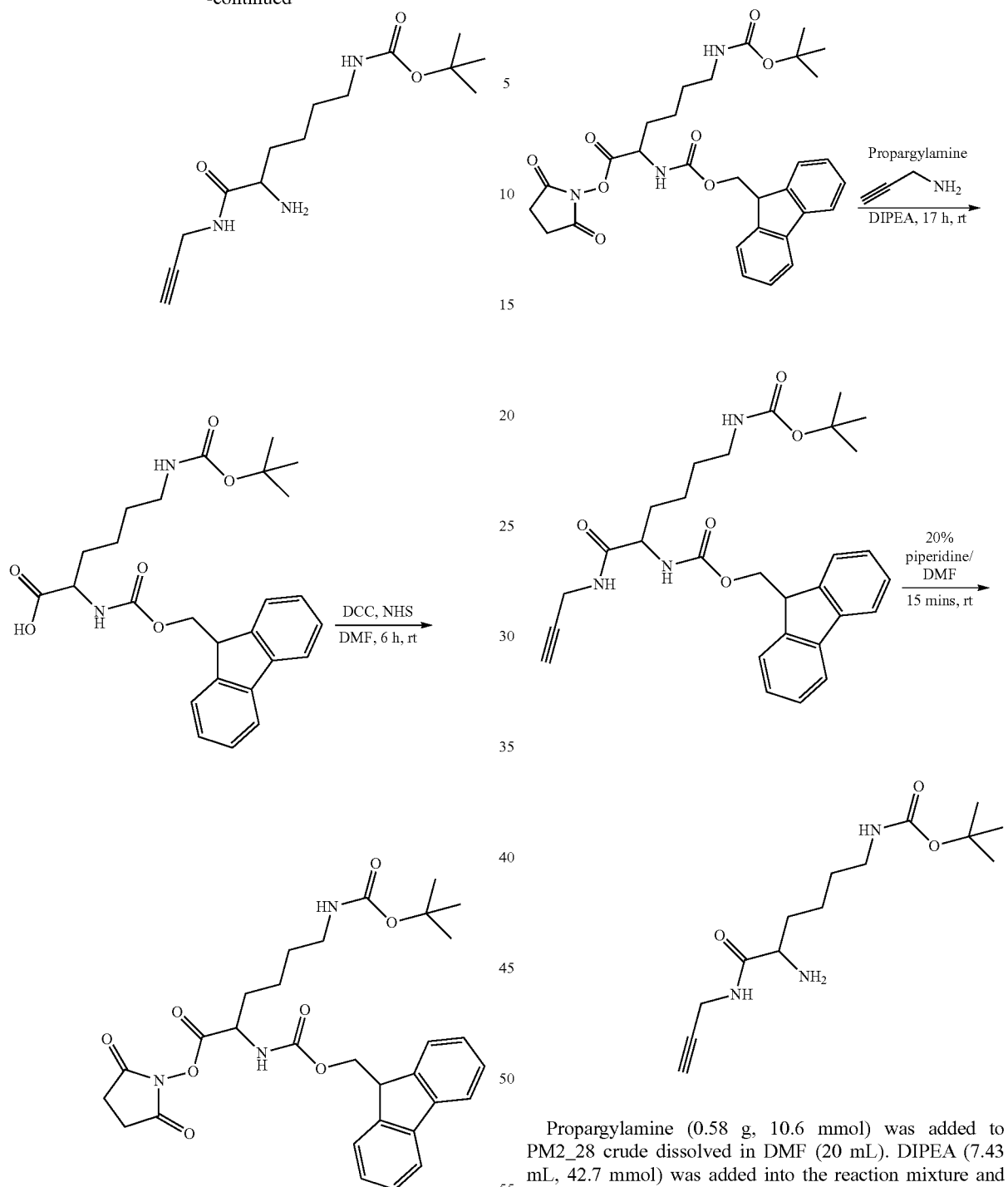

Fmoc-Lys(Boc)-OH (5 g, 10.6 mmol) was dissolved in DMF (20 mL). DCC (2.42 g, 11.7 mmol) and NHS (1.35 g, 11.7 mmol) were dissolved in DMF (15 mL) respectively and both were added to the reaction mixture. Reaction was stirred for 6 h at room temperature. After stirring, reaction mixture was filtered and solvents were removed under vacuo. Solid was dissolved in cold acetonitrile and DCM, filtration was done to remove the insoluble solid. Filtrate, PM2_28 was evaporated under vacuo and used immediately for the next step.

Propargylamine (0.58 g, 10.6 mmol) was added to PM2_28 crude dissolved in DMF (20 mL). DIPEA (7.43 mL, 42.7 mmol) was added into the reaction mixture and stirred overnight. After stirring, solvents were evaporated under vacuo and purified using flash chromatography to obtain a solid (0.94 g, 17%). The solid was dissolved in DMF (8 mL) and piperidine (2 mL) was added in. Reaction mixture was stirred for 15 min at room temperature. After stirring, reaction mixture was filtered and solvents were removed under vacuo. Crude was purified using flash chromatography to obtain a yellow oil, PM2_33 (0.54 g, quant.) $^1$H NMR (400 MHz, Chloroform-d) δ 1.40-1.34 (m, 2H), 1.43 (s, 9H), 1.56-1.47 (m, 4H), 2.21 (t, J=2.5 Hz, 1H), 3.11 (d, J=6.6 Hz, 2H), 3.36 (dd, J=8.0, 4.3 Hz, 1H), 4.04 (ddd, J=5.5, 2.6, 0.7 Hz, 2H). MS m/z 234.38 (M+H)$^+$.

Synthesis of PM2_97 (PS-Dab_Diol-Fl_ALK)
Target 1
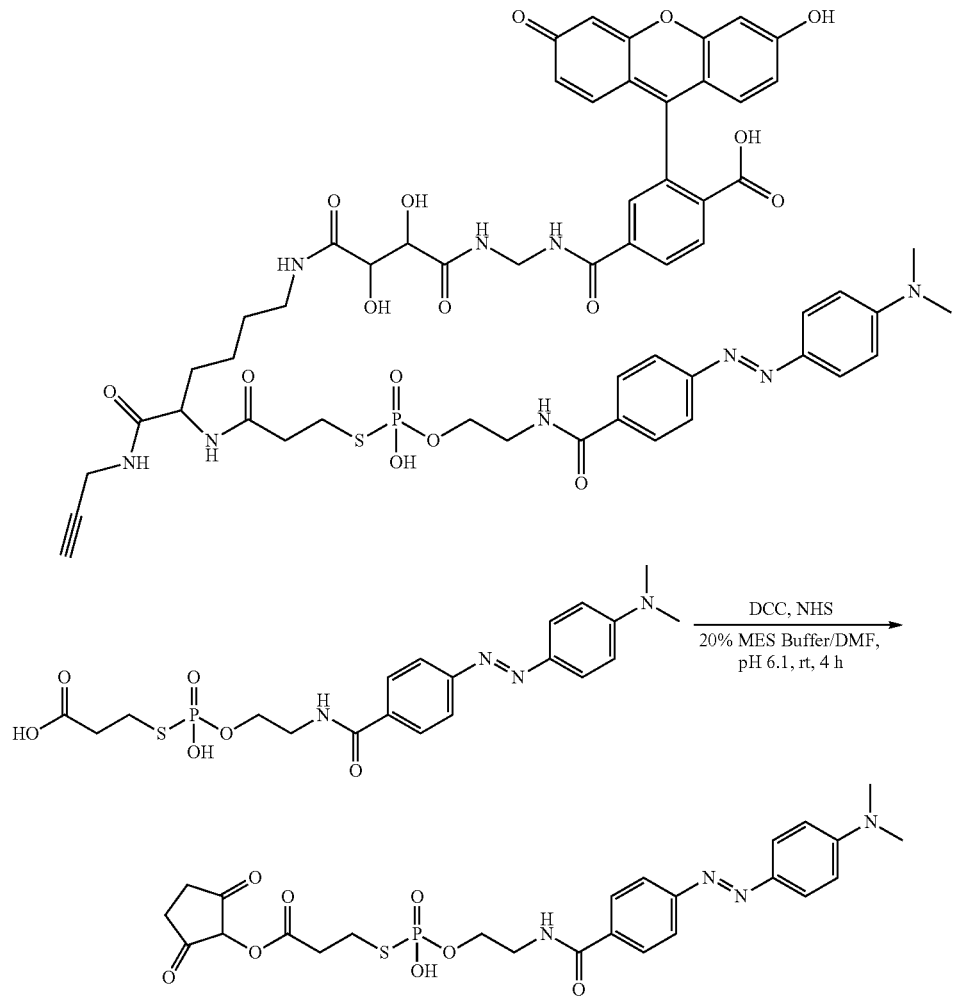
PS-Dab (9.5 mg, 19.8 umol) was dissolved in 20% 0.1 M MES buffer in DMF (5 mL). DCC (5.7 mg, 27.7 umol) and NHS (4 mg, 36.6 umol) were dissolved in DMF (1 mL) respectively and added into the reaction mixture. Reaction was stirred for 4 h at room temperature. After stirring, reaction mixture was filtered and NHS activated PS-Dab (PS-Dab-NHS) was obtained.
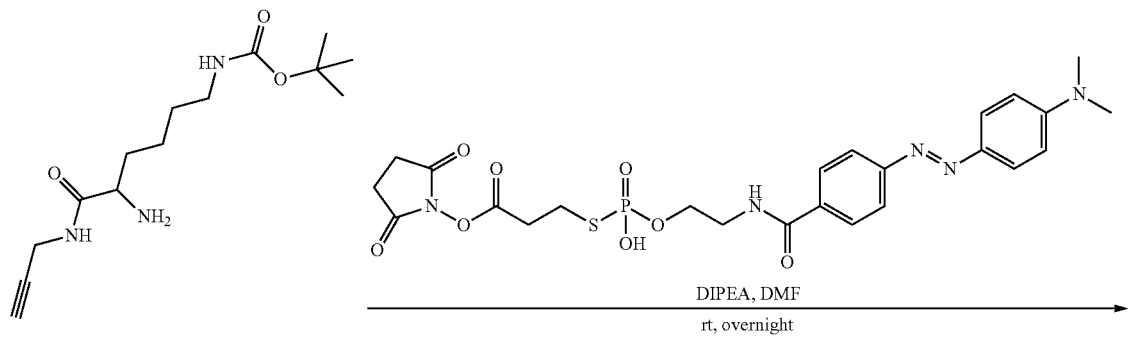

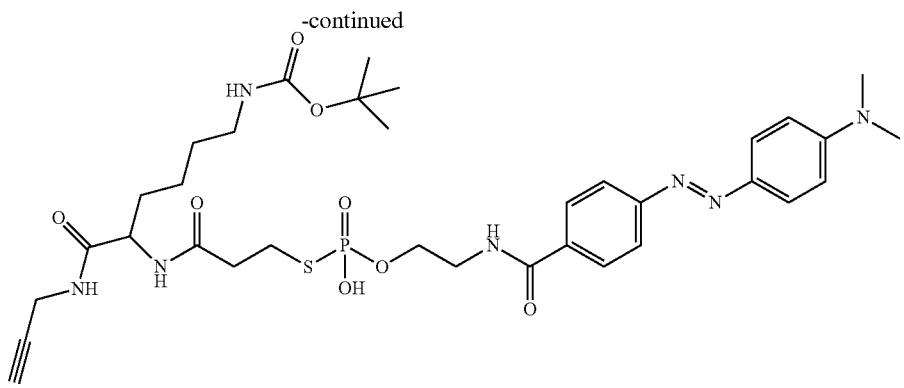

PM2_33 (5.6 mg, 19.8 umol) was dissolved in DMF (100 uL) and added into filtered PS-Dab-NHS. DIPEA (150 uL, 86.1 mmol) was added into the reaction mixture and stirred overnight. Solvents were removed under vacuo and crude was purified using HPLC to obtain an orange solid (7.3 mg, 50%), PM2_87. $^1$H NMR (400 MHz, Methanol-$d_4$) δ 1.42 (s, 9H), 1.43 (s, 4H), 1.65 (dd, J=9.2, 4.6 Hz, 1H), 1.73-1.87 (m, 1H), 2.53 (t, J=2.6 Hz, 1H), 2.64 (t, J=7.2 Hz, 2H), 2.94 (dd, J=14.4, 7.0 Hz, 2H), 3.01 (t, J=7.6 Hz, 2H), 3.11 (s, 6H), 3.68 (t, J=5.3 Hz, 2H), 3.93-3.95 (m, 2H), 4.11 (dt, J=8.4, 5.4 Hz, 2H), 4.27-4.31 (m, 1H), 6.84 (d, J=9.3 Hz, 2H), 7.85 (t, J=8.5 Hz, 4H), 7.99 (d, J=8.6 Hz, 2H). MS m/z 744.89 (M−H)$^−$.

PM2_87 (7.3 mg, 9.8 umol) was dissolved in DCM (2 mL) and MeOH (1 mL). Trifluoroacetic acid (1 mL) was added into the reaction mixture and turned pink. Reaction was stirred for 5 h. After stirring, triethylamine was added into the reaction mixture till it turned orange. Solvents were removed under vacuo and purified using HPLC to obtain an orange solid, PM2_92 (7 mg, quant.). $^1$H NMR (400 MHz, Methanol-$d_4$) δ 1.35-1.93 (m, 6H), 2.54 (dt, J=6.1, 2.5 Hz, 1H), 2.59-2.67 (m, 2H), 2.95 (dq, J=20.8, 7.3, 6.8 Hz, 2H), 3.11 (d, J=0.8 Hz, 6H), 3.62-3.71 (m, 2H), 3.95 (q, J=2.4 Hz, 2H), 4.11 (dt, J=8.3, 5.5 Hz, 2H), 4.50 (s, 3H), 6.80-6.88 (m, 2H), 7.81-7.89 (m, 4H), 7.99 (dq, J=8.8, 2.2 Hz, 2H). MS m/z 646.77 (M+H)$^+$.

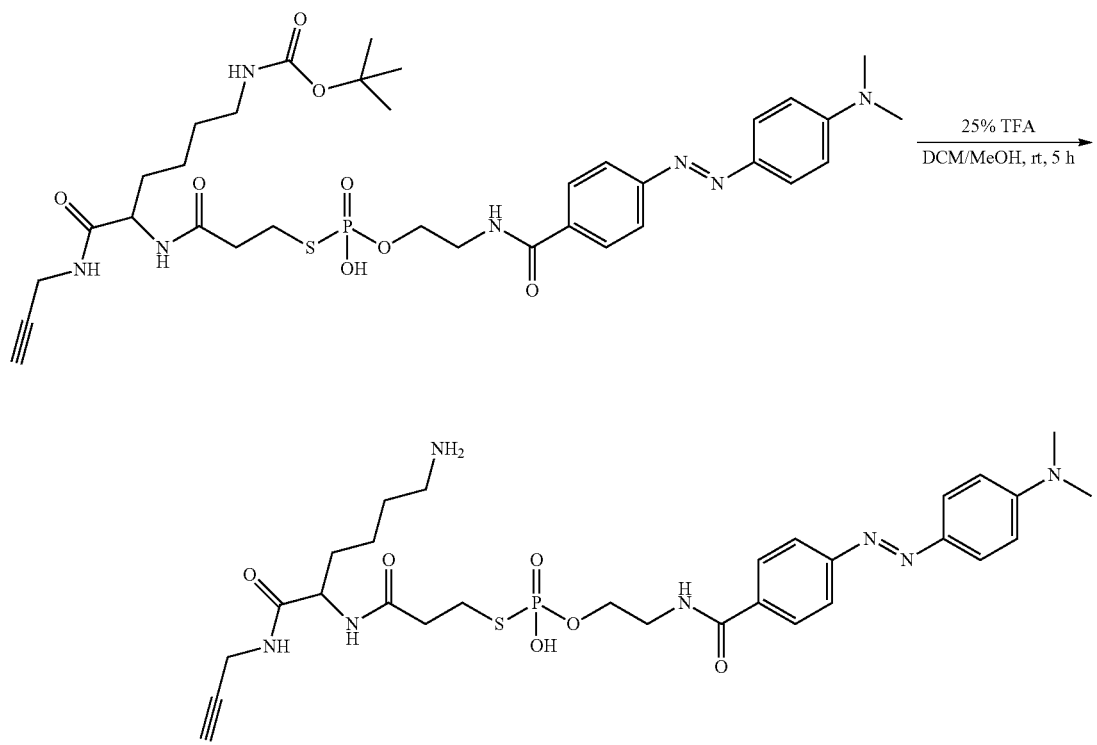

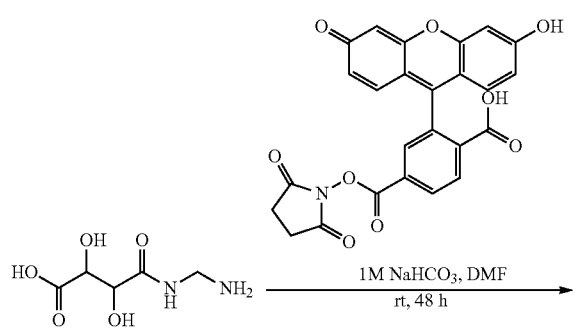
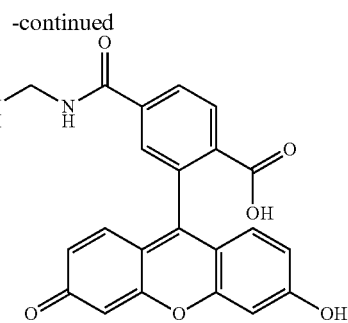

NHS-Fluorescein (53.1 mg, 112 umol) was dissolved in DMF (6 mL) and added to Diol linker (20 mg, 112 umol) in 1 M NaHCO₃ (6 mL). Reaction mixture was stirred for 48 h at room temperature. After stirring, solvents were removed under vacuo and purified with HPLC to obtain a yellow solid, Diol-Fluorescein (4 mg, 6.7%). MS m/z 537.11 (M+H)⁺.

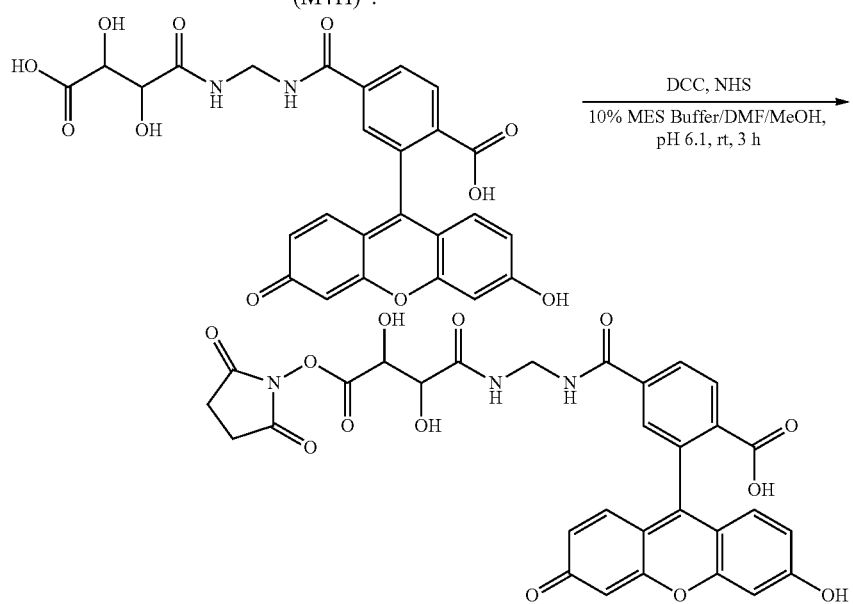

Diol-Fluorescein (9.5 mg, 19.8 umol) was dissolved in DMF (2 mL), 0.1 M MES buffer, pH 6.1 (200 uL) and MeOH (200 uL). DCC (2.15 mg, 10.4 umol) and NHS (1.54 mg, 13.4 umol) were dissolved in DMF (1 mL) respectively and added into the reaction mixture. Reaction was stirred for 3 h at room temperature. After stirring, reaction mixture was filtered and NHS activated Diol-Fluorescein (Diol-Fl-NHS) was obtained.

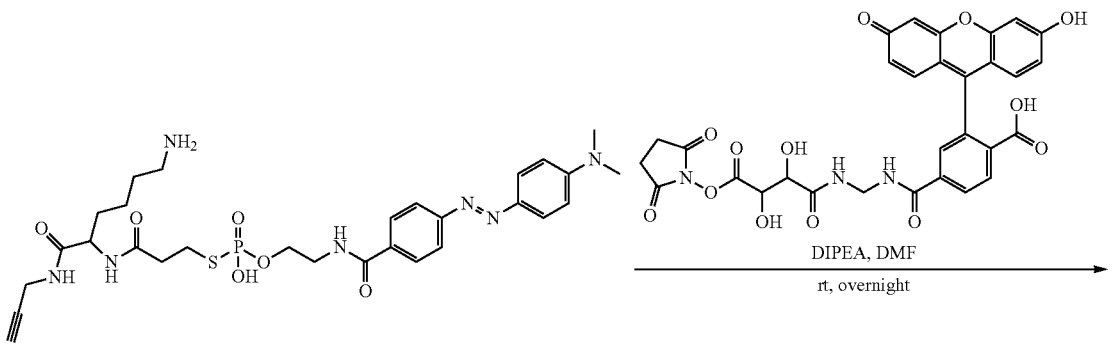

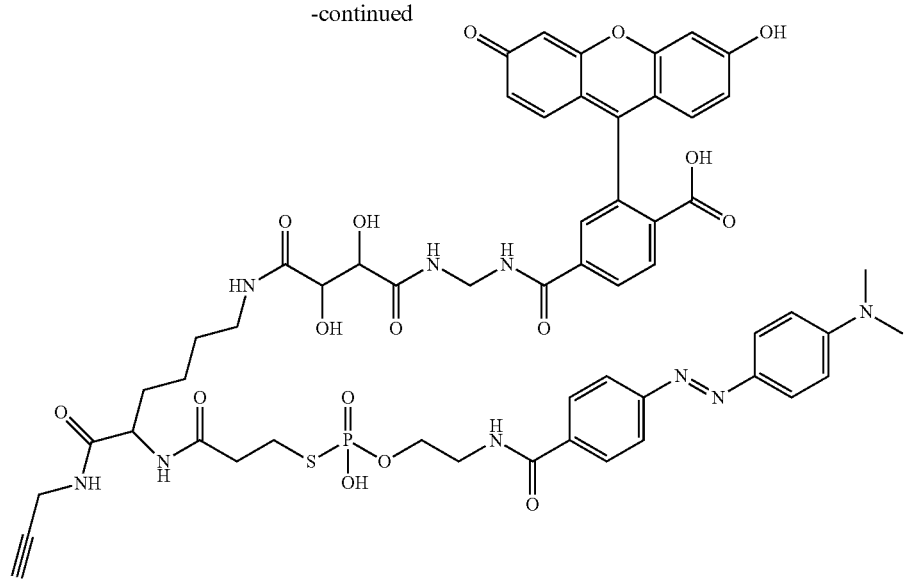
PM2_92 (4 mg, 6.2 umol) was dissolved in DMF (1 mL) and added into filtered Diol-Fl-NHS. DIPEA (150 uL, 86.1 mmol) was added into the reaction mixture and stirred overnight. After stirring, solvents were removed under vacuo and purified using HPLC to obtain product, PM2_97.
Synthesis of PM2_77 (SS-Dab_Si-Cy3_ALK)
Target 2
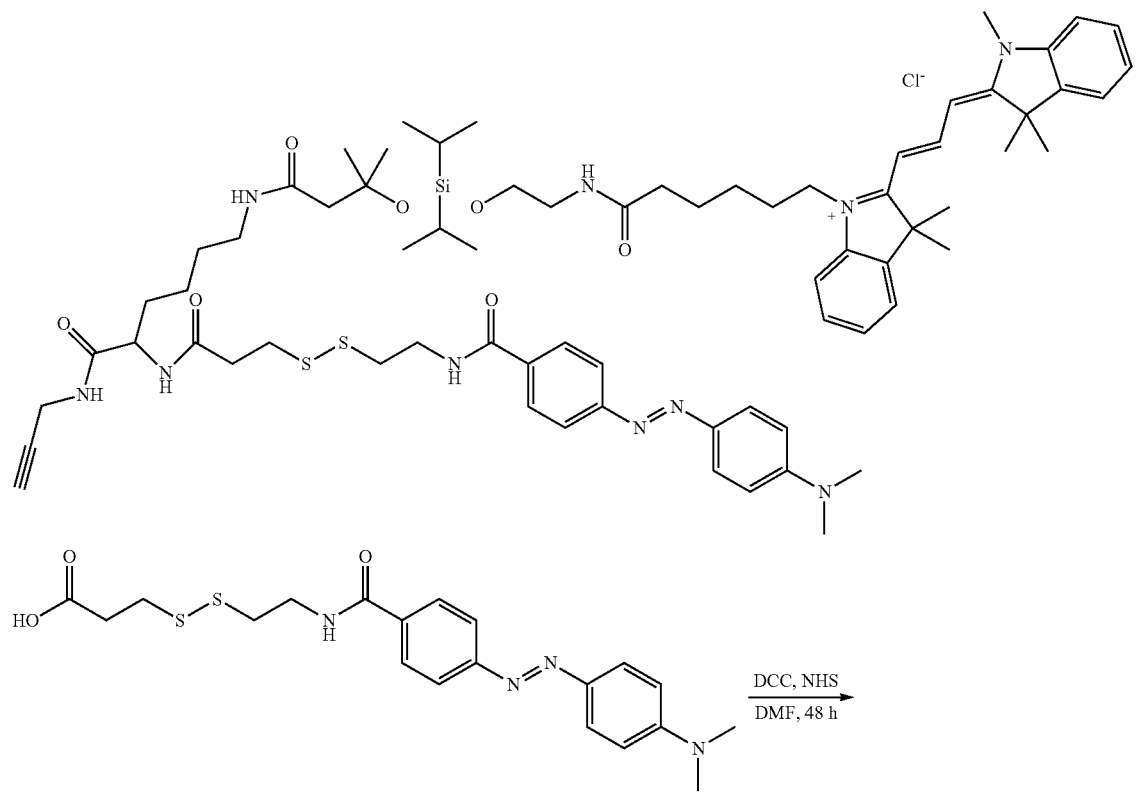

-continued

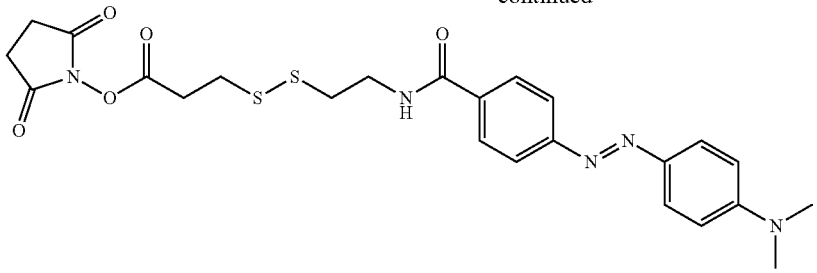

SS-Dab (20 mg, 46.3 umol) was dissolved in DMF (2 mL). DCC (13.4 mg, 64.8 umol) and NHS (9.6 mg, 83.3 umol) were dissolved in DMF (1 mL) respectively and added into the reaction mixture. Reaction was stirred for 48 h at room temperature. After stirring, reaction mixture was filtered and NHS activated SS-Dab (SS-Dab-NHS) was obtained.

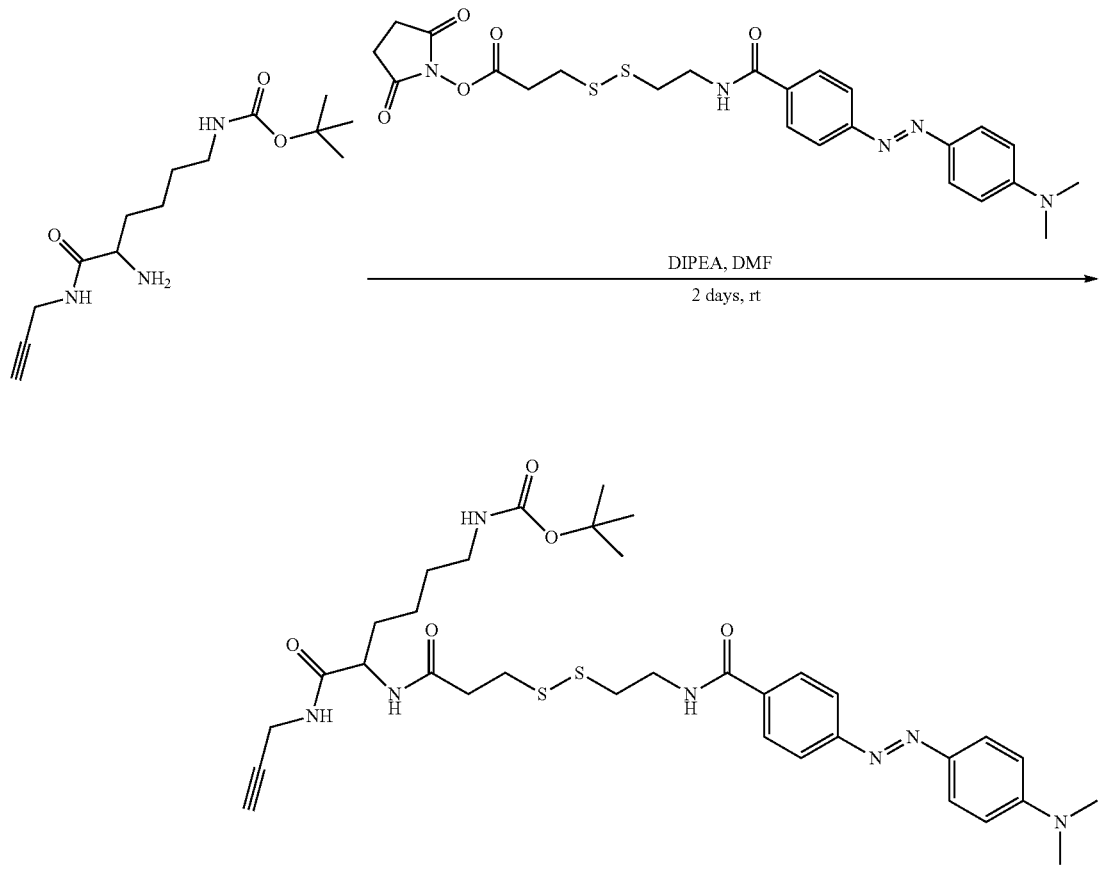

PM2_33 (13 mg, 46.3 umol) was added into filtered PS-Dab-NHS. DIPEA (32.2 uL, 18.5 mmol) was added into the reaction mixture and stirred for 48 h at room temperature. Solvents were removed under vacuo and crude was purified using flash chromatography to obtain an orange solid (7.1 mg, 22%), PM2_60. $^{13}$C NMR (101 MHz, CDCl$_3$) δ 171.71, 167.78, 156.54, 155.30, 153.04, 143.78, 134.32, 128.20, 125.54, 122.30, 111.63, 79.34, 77.48, 77.16, 76.84, 71.70, 71.70, 53.13, 53.12, 50.76, 40.37, 39.37, 38.17, 36.27, 34.67, 31.71, 29.80, 29.60, 29.27, 28.54, 22.70. MS m/z 698.87 (M+H)$^+$.

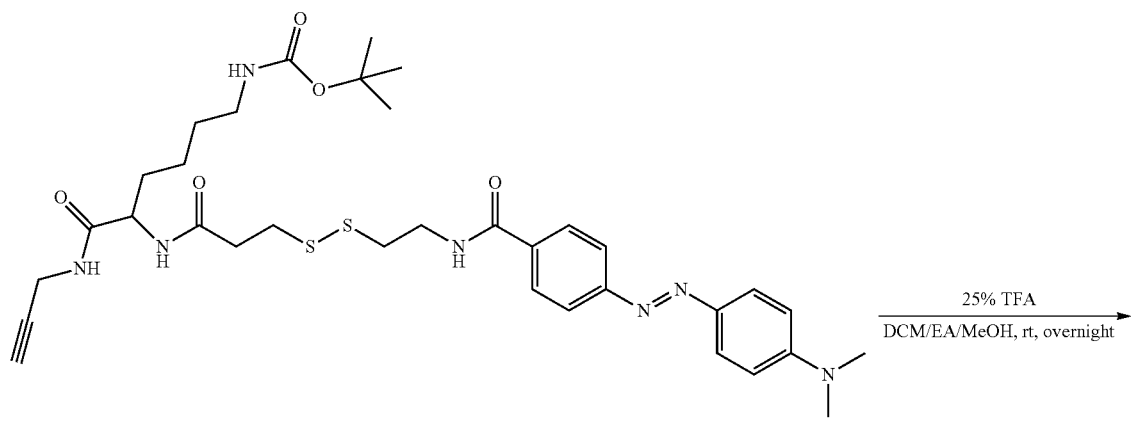

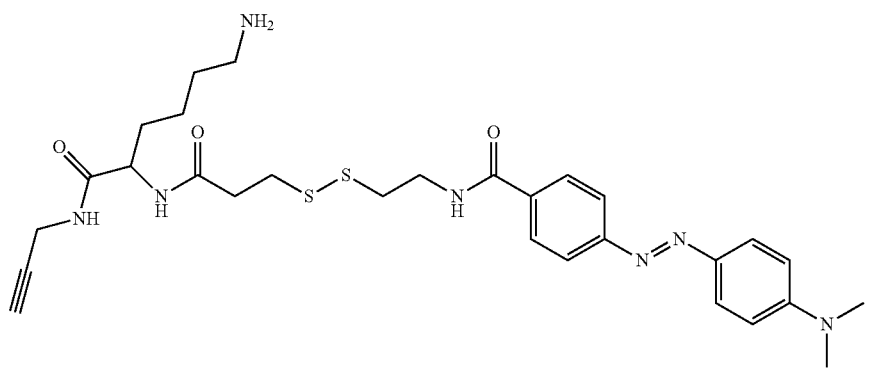

PM2_60 (3.5 mg, 5 umol) was dissolved in DCM (0.85 mL), Ethyl Acetate (0.45 mL) and MeOH (0.2 mL). Trifluoroacetic acid (0.5 mL) was added into the reaction mixture and turned pink. Reaction was stirred overnight. After stirring, 1 M NaHCO$_3$ was added into the reaction mixture till it turned orange. Extraction was done with DCM, wash with brine and dried over Na$_2$SO$_4$. Solvents were removed under vacuo and purified using HPLC to obtain an orange solid, PM2_71 (0.6 mg, 20%). MS m/z 598.60 (M+H)$^+$.

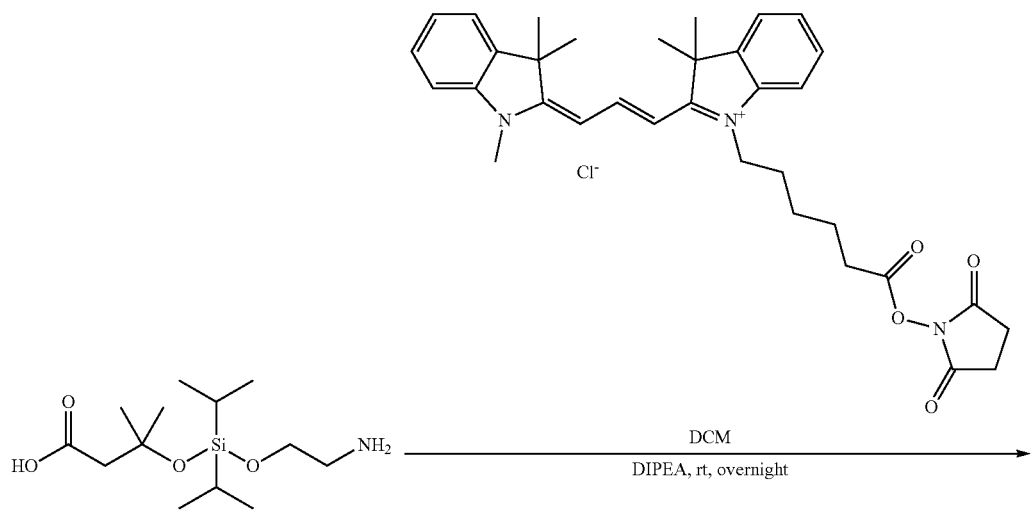

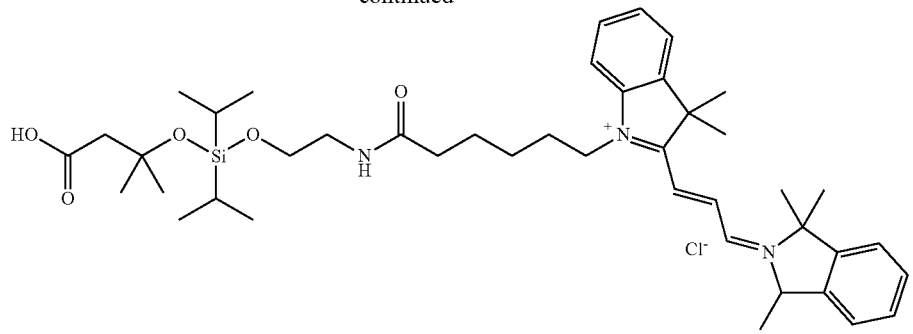

Cy3-ester (10 mg, 16.9 umol) was dissolved in DMF (4 mL) and added to Silyl linker (5 mg, 16.9 umol) in DMF (2 mL). DIPEA (5.26 mg, 40.7 umol) was added to the reaction mixture and was stirred for overnight at room temperature. After stirring, solvents were removed under vacuo and purified with flash chromatography to obtain a pink solid, Si-Cy3 (8.7 mg, 67%). $^1$H NMR (400 MHz, Chloroform-d) δ 0.77-0.83 (m, 3H), 0.94 (d, J=5.9 Hz, 9H), 1.19 (s, 6H), 1.64-1.67 (m, 12H), 1.73-1.90 (m, 11H), 2.26 (t, J=7.3 Hz, 2H), 2.38 (s, 1H), 2.63 (s, 1H), 3.28-3.37 (m, 2H), 3.72-3.78 (m, 4H), 4.04-4.18 (m, 2H), 6.94-7.11 (m, 3H), 7.13 (d, J=2.7 Hz, 1H), 7.26-7.37 (m, 4H). MS m/z 767.08 (M+H)$^+$.

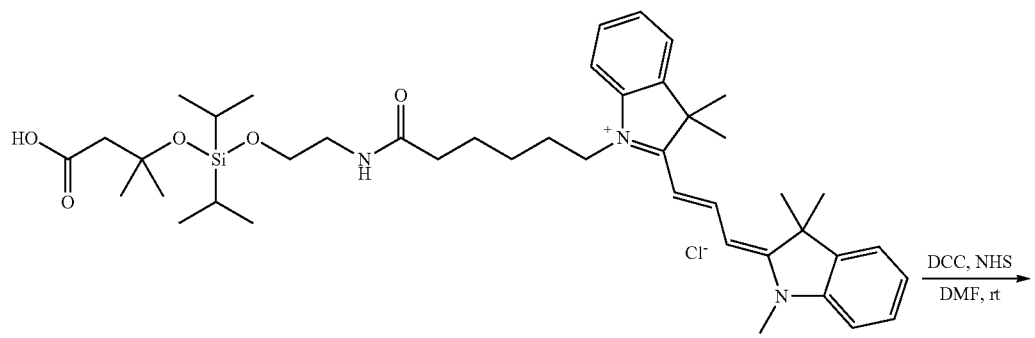

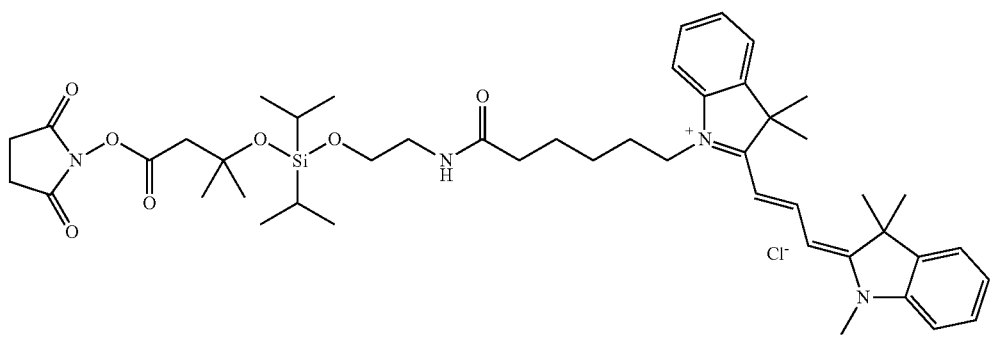

Si-Cy3 (0.8 mg, 1 umol) was dissolved in anhydrous DCM (400 uL). DCC (0.3 mg, 1.46 umol) and NHS (0.2 mg, 1.88 umol) were dissolved in DMF (1 mL) respectively and added into the reaction mixture. Reaction was stirred overnight at room temperature. After stirring, reaction mixture was filtered and NHS activated Si-Cy3 (Si-Cy3-NHS) was obtained.

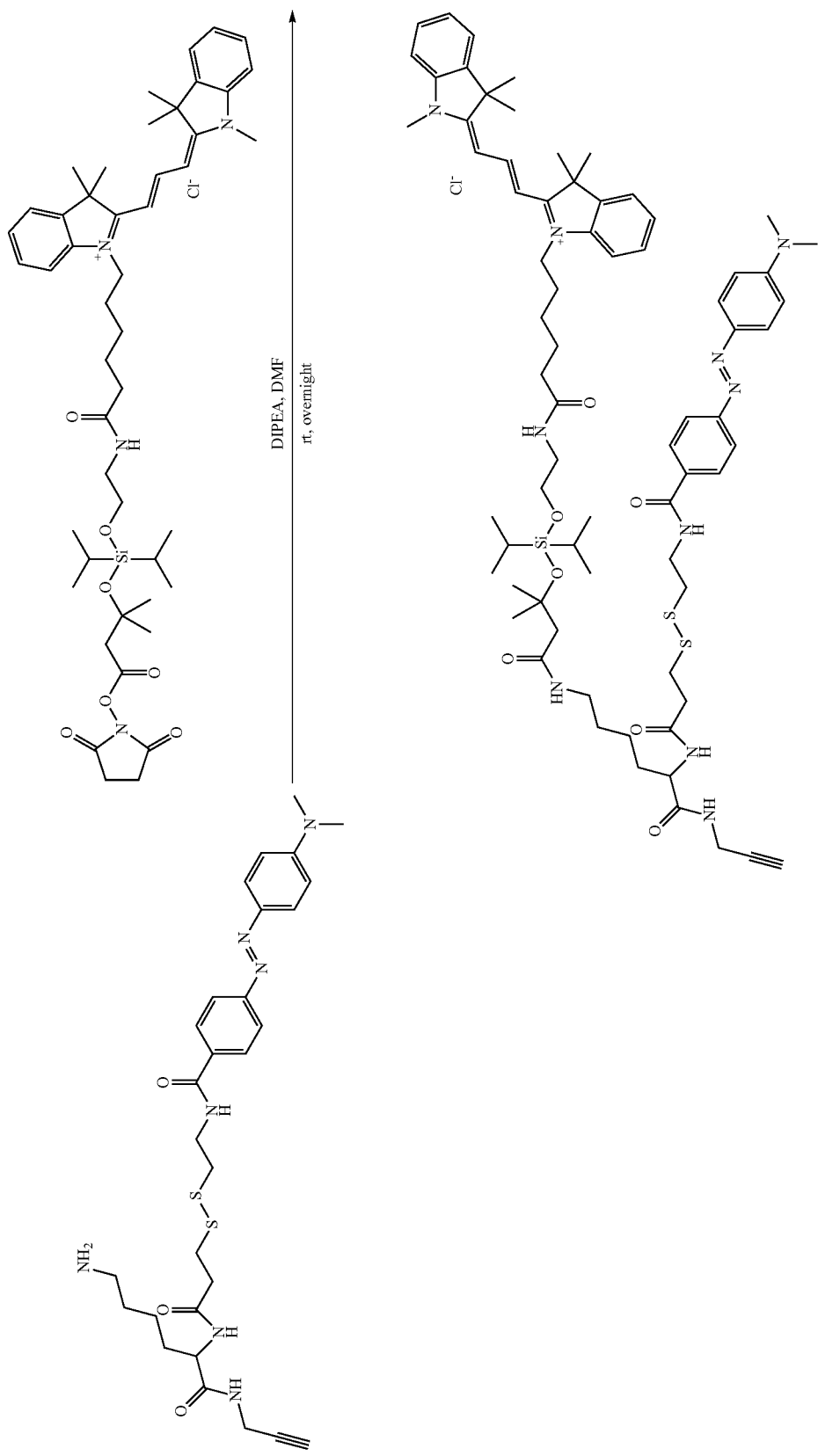

PM2_71 (0.6 mg, 1 umol) was added into filtered Si-Cy3-NHS. DIPEA (10 uL, 57 umol) was added into the reaction mixture and stirred overnight. After stirring, solvents were removed under vacuo and purified using HPLC to obtain product, PM2_77.

Targets with Cleavable Linkers Directly Attached on Oligos

PS-Dab-Diol-Pyrene-5'-5' Oligo Seq 4 (PM2_20)

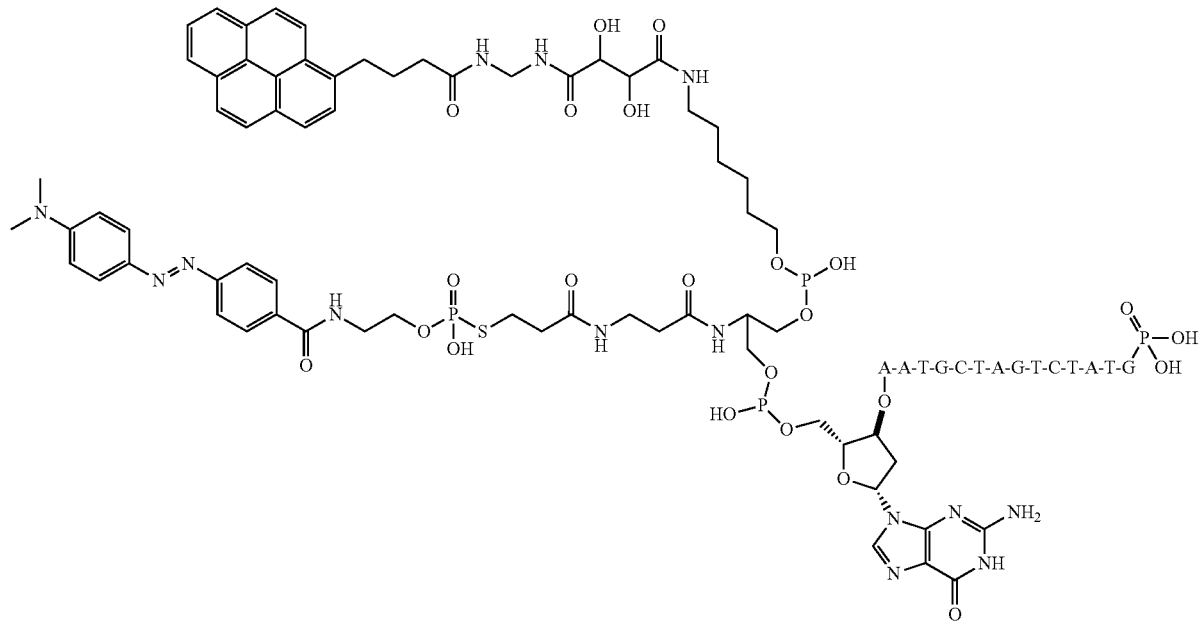

Oligo sequence: 5'-(DMS(O)MT Amino modifier)-(Amino-modifier serinol)-GAATG CTAGT CTATG-3'

PS-Dab (1.44 mg, 3 umol) was dissolved in DMF (400 uL). DCC (0.74 mg, 3.59 umol) and NHS (0.45 mg, 3.91 umol) were dissolved in DMF (100 uL) respectively and added into the reaction mixture. Reaction was stirred for 2 h and filtered. A NHS-activated PS-Dab was obtained.

Diol-Pyrene (1.34 mg, 3 umol) was dissolved in DMF (400 uL). DCC (0.74 mg, 3.59 umol) and NHS (0.45 mg, 3.91 umol) were dissolved in DMF (100 uL) respectively and added into the reaction mixture. Reaction was stirred for 2 h and filtered. A NHS-activated Diol-Pyrene was obtained.

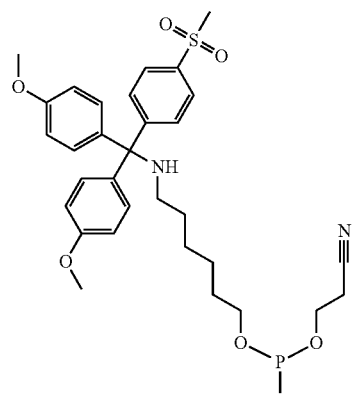

1) 10% DEA/ACN, 5 min
2) 20% piperidine/DMF, 15 min

-continued
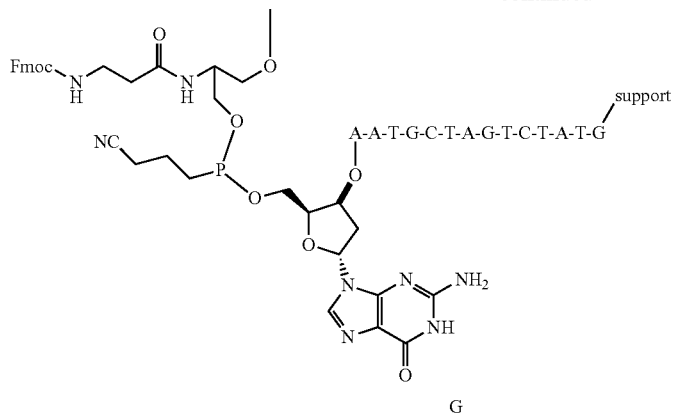
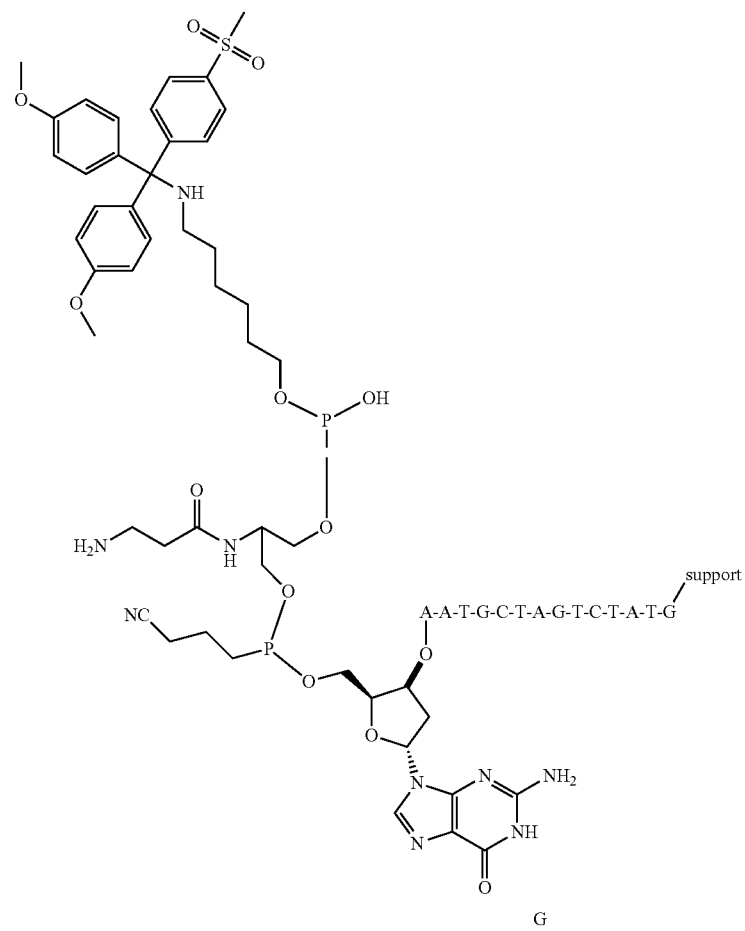

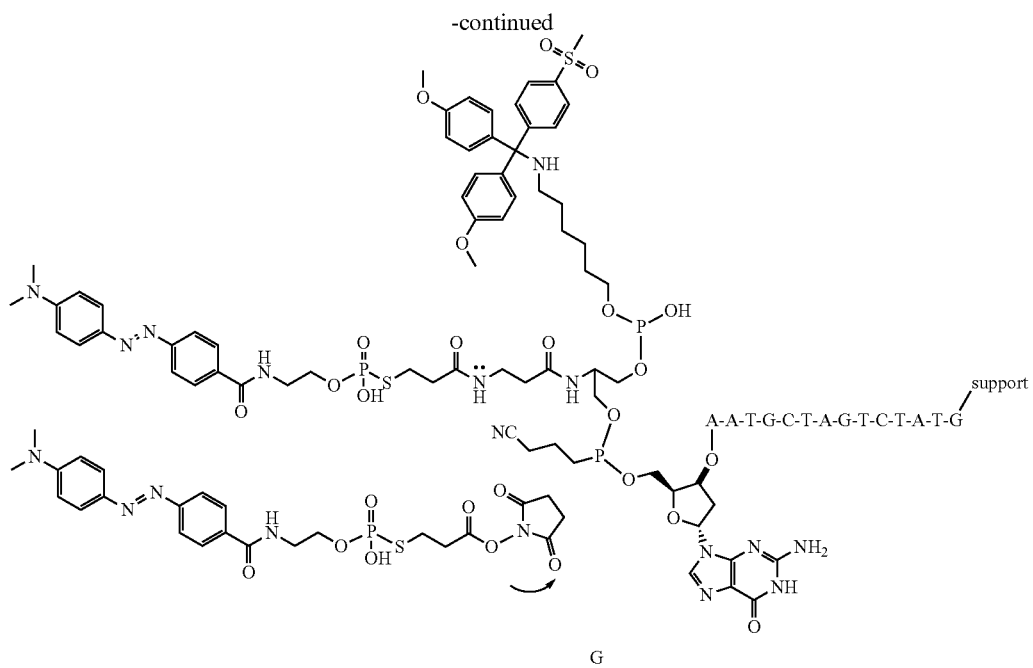

CPG column was flushed with 10% diethylamine in acetonitrile (1 mL) for 5 min and rinsed with low water acetonitrile (10 mL). CPG column was flushed to and fro with 20% piperidine/DMF (2.5 mL) using 2 syringes and left to stand for 5 min. This step was repeated for 3 times. The CPG column was rinsed with DMF (3 mL) thrice and with low water acetonitrile (3 mL) thrice. CPG column was dried with Argon.

CPG support was transferred out to a 1.5 mL eppendorf tube. DMF (140 uL) and DIPEA (10 uL) were added into the tube and mixed gently. NHS-activated PS-Dab was added into the tube and reaction was incubated for 2 h at room temperature. After incubation, tube was centrifuged and supernatant was removed. CPG support was rinsed with DMF (1 mL), tube was centrifuged and supernatant was removed. This step was repeated 3 times. CPG support was rinsed with acetonitrile (1 mL), tube was centrifuged and supernatant was removed. This step was repeated 3 times. CPG support was transferred back to the column. CPG column was flushed with Dichloromethane (DCM) (1 mL) thrice. CPG column was dried with Argon.

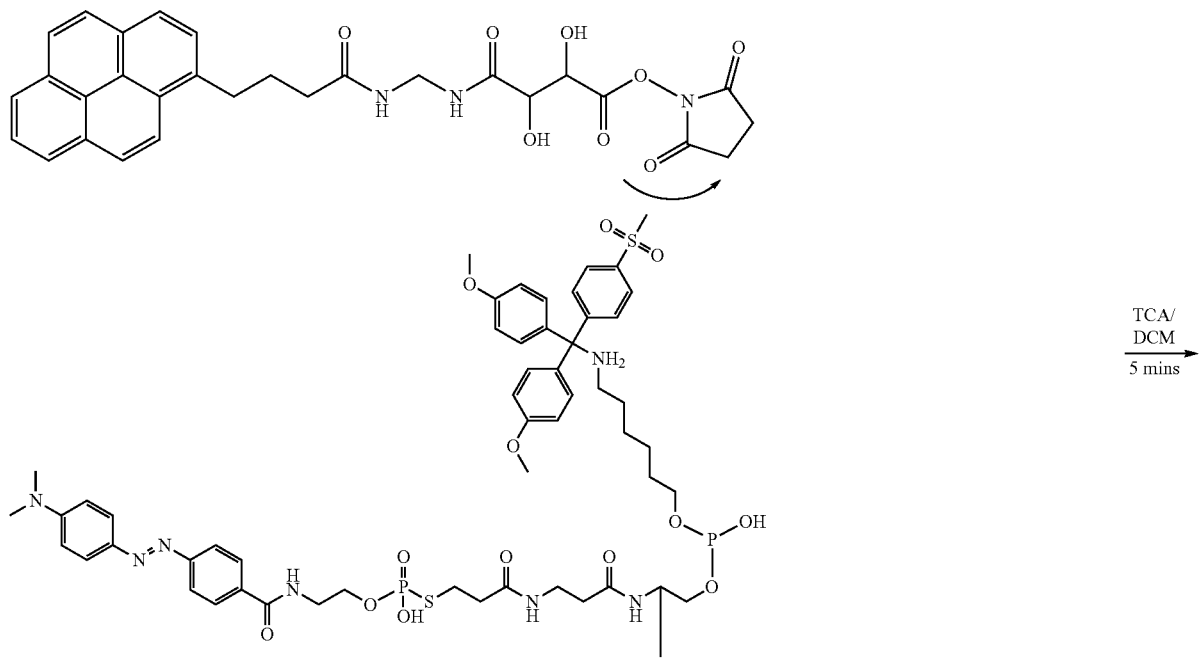

-continued

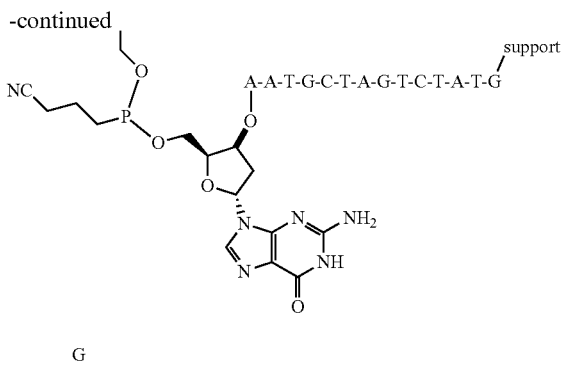

G

CPG column was placed on ABI 394 DNA/RNA synthesizer and 3% trichloroacetic acid/dichloromethane (DCM) was passed through the column for 100 s. CPG column was rinsed with DCM for 40 s, acetonitrile for 40 s and reverse flush for 20 s. CPG column was dried with Argon.

CPG support was transferred out to a 1.5 mL eppendorf tube. DMF (140 uL) and DIPEA (10 uL) were added into the tube and mixed gently. NHS-activated Diol-Pyrene was added into the tube and reaction was incubated for 2 h at room temperature. After incubation, tube was centrifuged and supernatant was removed. CPG support was rinsed with DMF (1 mL), tube was centrifuged and supernatant was removed. This step was repeated 3 times. CPG support was rinsed with acetonitrile (1 mL), tube was centrifuged and supernatant was removed. This step was repeated 3 times. CPG support was transferred back to the column. CPG column was flushed with DCM (1 mL) thrice. CPG column was dried with Argon.

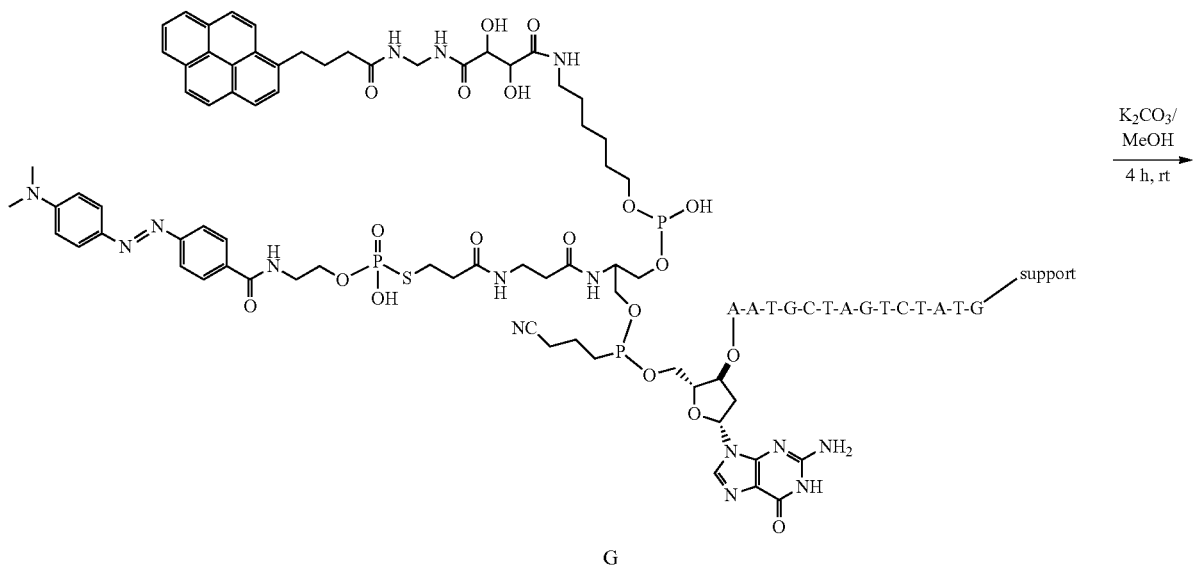

G

Figure 6:
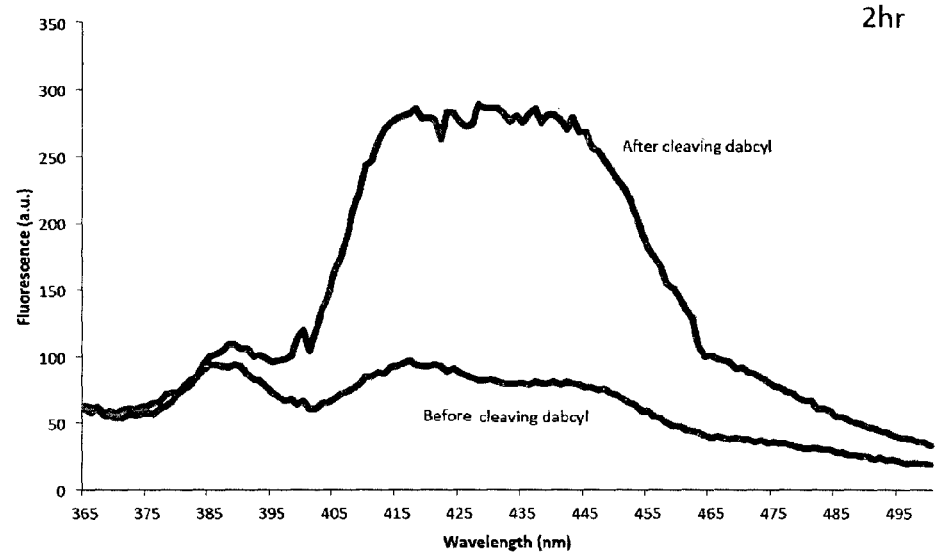
FIG. 6 shows the fluorescence emission spectra of a fluoromodule after cleavage of the phosphorothioate-linker quencher according to one example.

Oligo sequence was cleaved from CPG support with 0.05 M potassium carbonate in methanol for 4 h at room temperature. HPLC purification was done on the oligo sequence and PM2_20 was obtained. The increase in fluorescence upon cleavage of the phosphorothioate-linked quencher is validated and shown in FIG. 6.

Si-Pyrene-SS-Dab-5'-5' Oligo Seq 3 (PM2_24)

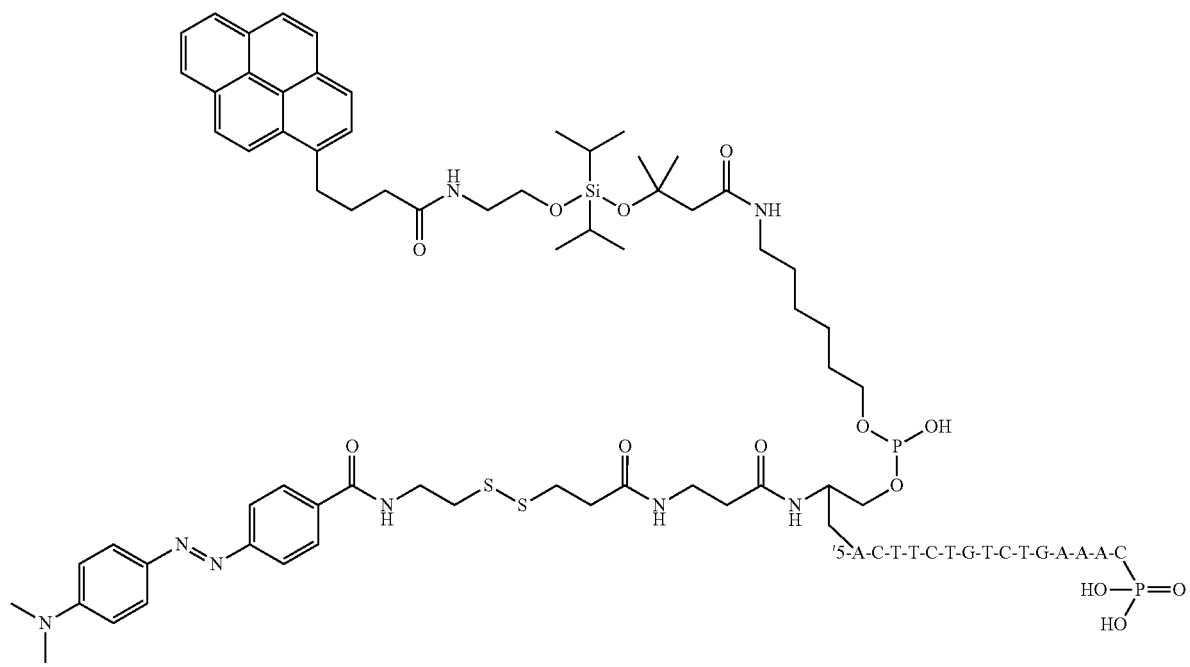

Oligo sequence: 5'-(DMS(O)MT Amino modifer)-(Amino-modifier serinol)-ACTTC TGTCT GAAAC-3'

Si-Pyrene (1.69 mg, 3 umol) was dissolved in DMF (400 uL). DCC (0.74 mg, 3.59 umol) and NHS (0.45 mg, 3.91 umol) were dissolved in DMF (100 uL) respectively and added into the reaction mixture. Reaction was stirred for overnight and filtered. A NHS-activated Si-Pyrene was obtained.

CPG column was flushed with 10% diethylamine in acetonitrile (1 mL) for 5 min and rinsed with low water acetonitrile (10 mL). CPG column was placed on ABI 394 DNA/RNA synthesizer and 3% trichloroacetic acid/DCM was passed through the column for 100 s. CPG column was rinsed with DCM for 40 s, acetonitrile for 40 s and reverse flush for 20 s. CPG column was dried with Argon.

CPG support was transferred out to a 1.5 mL eppendorf tube. DMF (140 uL) an DIPEA (10 uL) were added into the tube and mixed gently. NHS-activated Si-Pyrene was added into the tube and reaction was incubated for 2 h at room temperature. After incubation, tube was centrifuged and supernatant was removed. CPG support was rinsed with DMF (1 mL), tube was centrifuged and supernatant was removed. This step was repeated 3 times. CPG support was rinsed with acetonitrile (1 mL), tube was centrifuged and supernatant was removed. This step was repeated 3 times. CPG support was transferred back to the column. CPG column was flushed with Dichloromethane (DCM) (1 mL) thrice. CPG column was dried with Argon.

CPG column was flushed to and fro with 20% piperidine/DMF (2.5 mL) using 2 syringes and left to stand for 5 min. This step was repeated for 3 times. The CPG column was rinsed with DMF (3 mL) thrice and with low water acetonitrile (3 mL) thrice. CPG column was dried with Argon.

SS-Dab (1.30 mg, 3 umol) was dissolved in DMF (400 uL). DCC (0.74 mg, 3.59 umol) and NHS (0.45 mg, 3.91 umol) were dissolved in DMF (100 uL) respectively and added into the reaction mixture. Reaction was stirred for overnight and filtered. A NHS-activated SS-Dab was obtained.

Oligo sequence with Si-Pyrene attached was cleaved from CPG support with 0.05 M potassium carbonate in methanol for 4 h at room temperature. Oligo sequence in solution was concentrated to 200 uL. Oligo sequence was extracted with chloroform (200 uL) thrice and precipitated with 3 M NaCl (20 uL) and cold absolute ethanol (500 uL). Oligo sequence was mixed well and incubated at −20° C. for 30 min and centrifuged at 12,000 g for 30 min. Supernatant was removed and pellet was rinsed twice with cold 70% ethanol and dried briefly.

Figure 7:
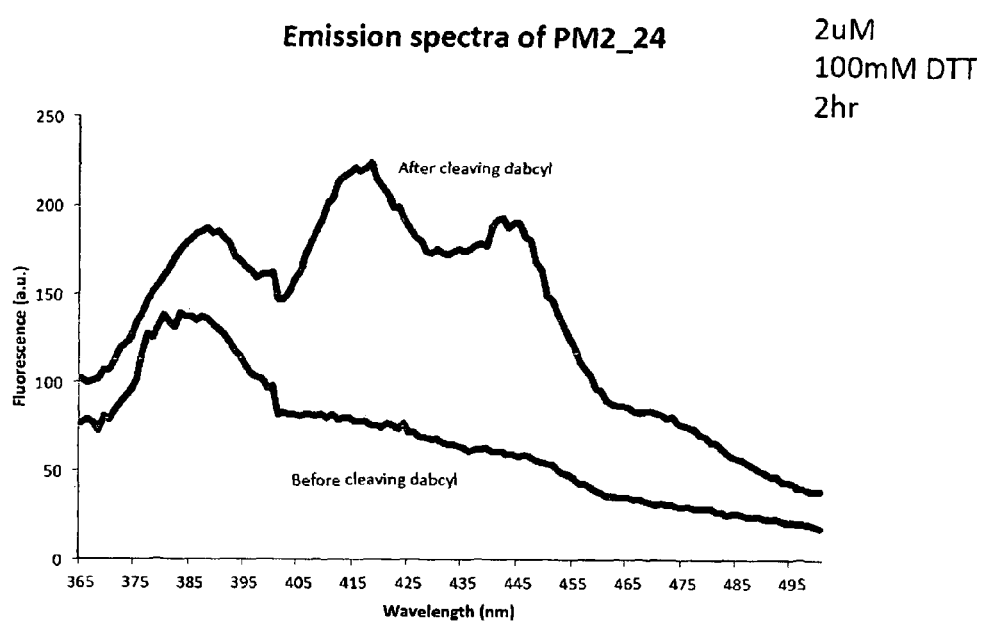
FIG. 7 shows the fluorescence emission spectra of a fluoromodule after cleavage of the silyl-linker quencher according to one example.

Pellet obtained was dissolved in sodium tetraborate, pH 8.5 (300 uL). NHS activated SS-Dab was added and stirred for 2 h. HPLC purification was done on the oligo sequence and PM2_24 was obtained. The increase in fluorescence upon cleavage of the silyl-linked quencher is validated and shown in FIG. 7.

Cleavable Experiments

Diol Linker

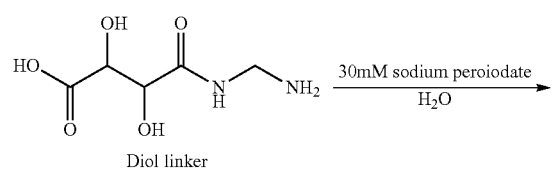

Diol linker

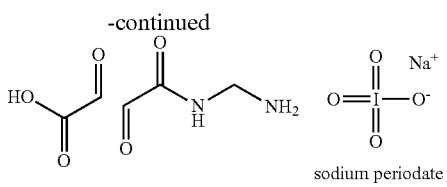

sodium periodate 60 mM sodium periodate in water (50 uL, 3 umol) was added to 20 mM Diol Linker in water (50 uL, 1 umol) and incubated for 2 h at room temperature. Reaction mixture was ran through an analytical C18 column with a LC-MS to monitor the cleavage reaction.

Silyl Linker

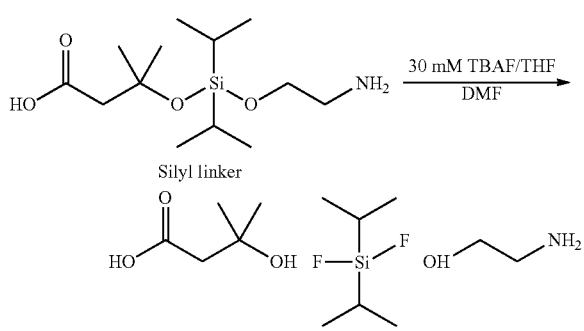

60 mM TBAF/THF (tetrabutylammonium fluoride/tetrahydrofuran) (50 uL, 3 umol) was added to 20 mM Silyl Linker in water (50 uL, 1 umol) and incubated for 2 h at room temperature. Reaction mixture was ran through an analytical C18 column with a LC-MS to monitor the cleavage reaction.

Phosphorothioate Linker

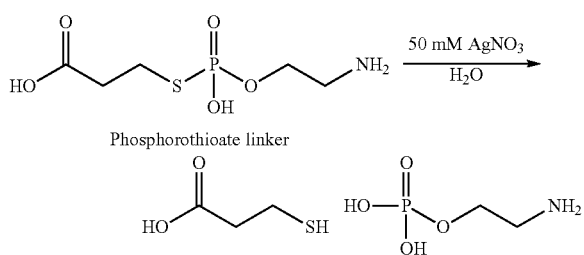

100 mM aqueous AgNO$_3$ (silver nitrate) (50 uL, 5 umol) was added to 20 mM Phosphorothioate Linker in water (50 uL, 1 umol) and incubated for 2 h at room temperature. Reaction mixture was ran through an analytical C18 column with a LC-MS to monitor the cleavage reaction.

Disulfide Linker

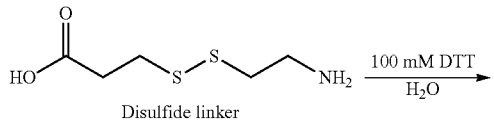

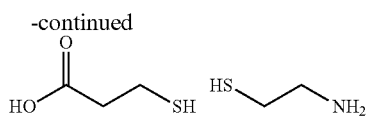

200 mM aqueous DTT (Dithiothreitol) (50 uL, 10 umol) was added to 20 mM Disulfide Linker in water (50 uL, 1 umol) and incubated for 2 h at room temperature. Reaction mixture was ran through an analytical C18 column with a LC-MS to monitor the cleavage reaction.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in teems of any individual member or subgroup of members of the Markush group.

The invention claimed is:

1. Fluorochrome-quencher conjugate having the structure

F-L1-B-L2-Q wherein
F is at least one fluorochrome;
Q is at least one quenching molecule for the at least one fluorochrome, or is another fluorochrome F, or is another fluorochrome other than F;
L1 is at least one first cleavable linker molecule;

L2 is at least one second cleavable linker molecule, wherein said L1 and L2 are different so that fluorophores can be selectively turned on upon specific cleavage of said L1 and L2; and B is a linking moiety or a target molecule of interest;

wherein L2 is directly attached to Q via amide coupling to form part of a modular system of the conjugate.

2. The conjugate of claim 1, wherein each of the at least one first cleavable linker and the at least one second cleavable linker is independently selected from the group consisting of azido linker, allyl linker, disulfide linker, phosphorothioate linker, diol linker, diazobenzene linker, acylsulfonamide linker, and silyl linker.

3. The conjugate of claim 2, wherein the at least one first and/or the at least one second cleavable linker are independently selected from the group consisting of:

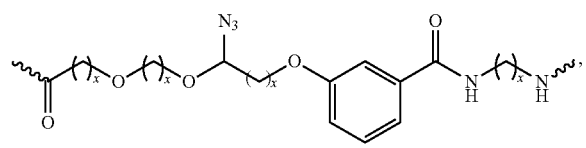

(azido linker)

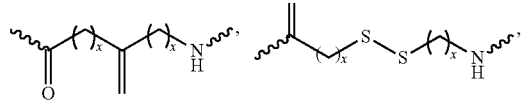

(allyl linker)          (disulfide linker)

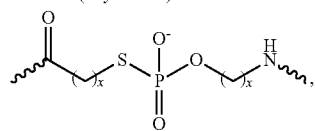

(phosphorothioate linker)

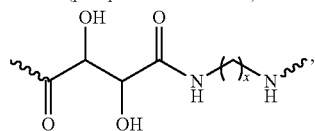

(diol linker)

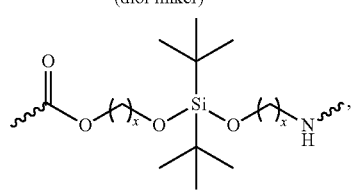

(silyl linker)

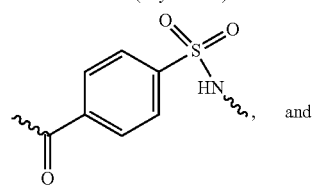

and (acylsulfonamide linker)

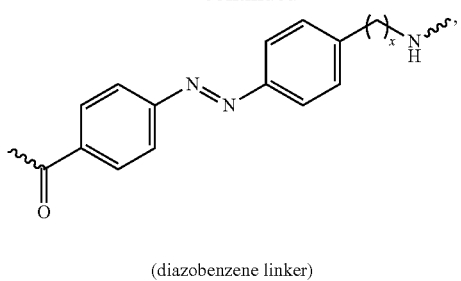

(diazobenzene linker)

wherein x is independently selected and is an integer of between 1 and 10.

4. The conjugate of claim 1, wherein the at least one fluorochrome is a fluorophore selected from the group consisting of Cy3, Cy5, FAM, TET, HEX, TMR, ROX, Texas red, LC red 640, and LC red 70.

5. The conjugate of claim 1, wherein the at least one quenching molecule is selected from the group consisting of QSY-7, DDQ-I, Dabcyl, Eclipse, Iowa Black FQ, BHQ-1, BHQ-2, DDQ-II, Iowa Black RQ, QSY-21, and BHQ-3.

6. The conjugate of claim 1, wherein Q is another fluorochrome other than F, wherein Q undergoes Forster resonance energy transfer (FRET) with F such that a fluorescence emission wavelength change occurs upon removal of Q.

7. The conjugate of claim 6, wherein the another fluorochrome other than F is Cy3 and Q is Cy5.

8. The conjugate of claim 5, wherein F is Cy3 and Q is QSY-7.

9. The conjugate of claim 1, wherein F, B, L1 and L2 are coupled to each other through conjugation chemistry.

10. The conjugate of claim 9, wherein F, B, L1 and L2 are coupled to each other by amide chemistry to form the modular system of the conjugate.

11. The conjugate of claim 1, wherein L1-F and L2-Q are separately conjugated to a respective biomolecule and are spaced at a distance apart for quenching of the fluorescence or FRET to occur.

12. The conjugate of claim 11, wherein the biomolecule is selected from the group consisting of nucleic acids, lipids, peptides and proteins.

13. The conjugate of claim 1, wherein B is a linking moiety and further comprises a reactive group R for coupling the conjugate to a target molecule.

14. The conjugate of claim 13, wherein B has the structure:

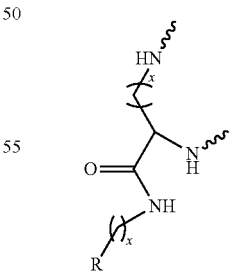

wherein R is selected from the group consisting of hydroxyl, carboxyl, and amine; and wherein x is independently selected and is an integer of between 1 and 6.

15. The conjugate of claim 1, wherein the target molecule is an amino acid, a peptide, a polypeptide, a nucleotide, an oligonucleotide, or a polynucleotide.

16. The conjugate of claim 1, wherein the conjugate is
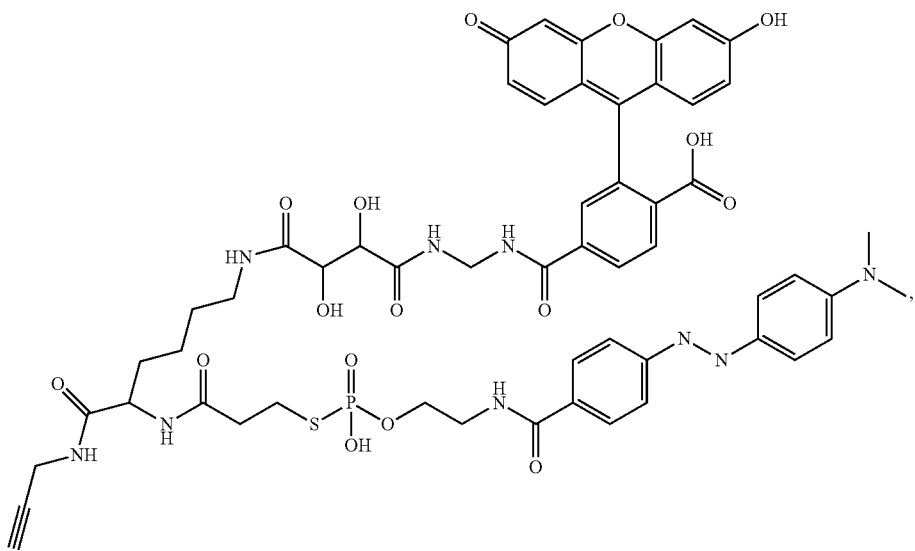
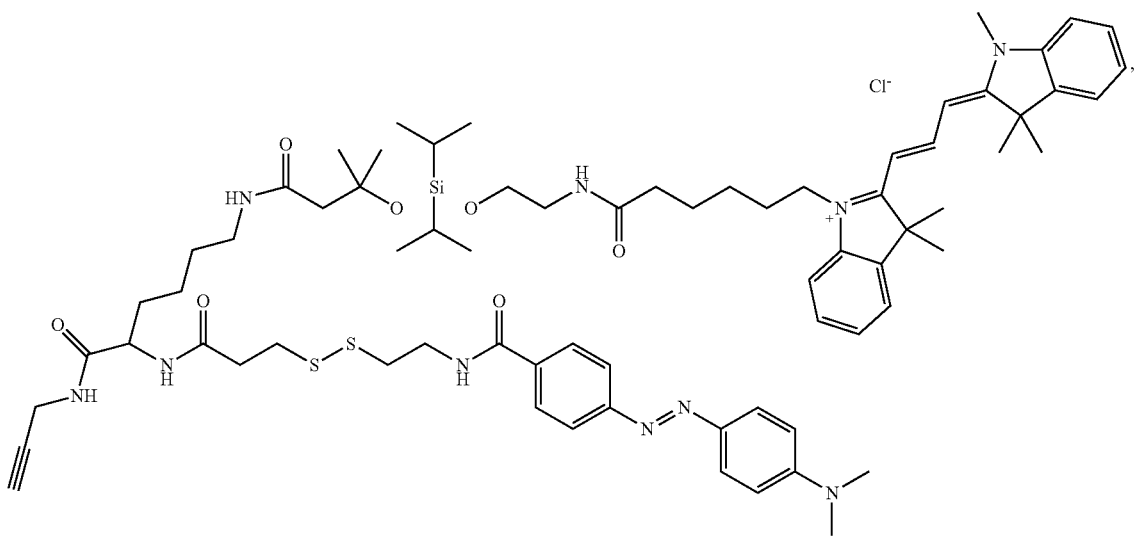

-continued

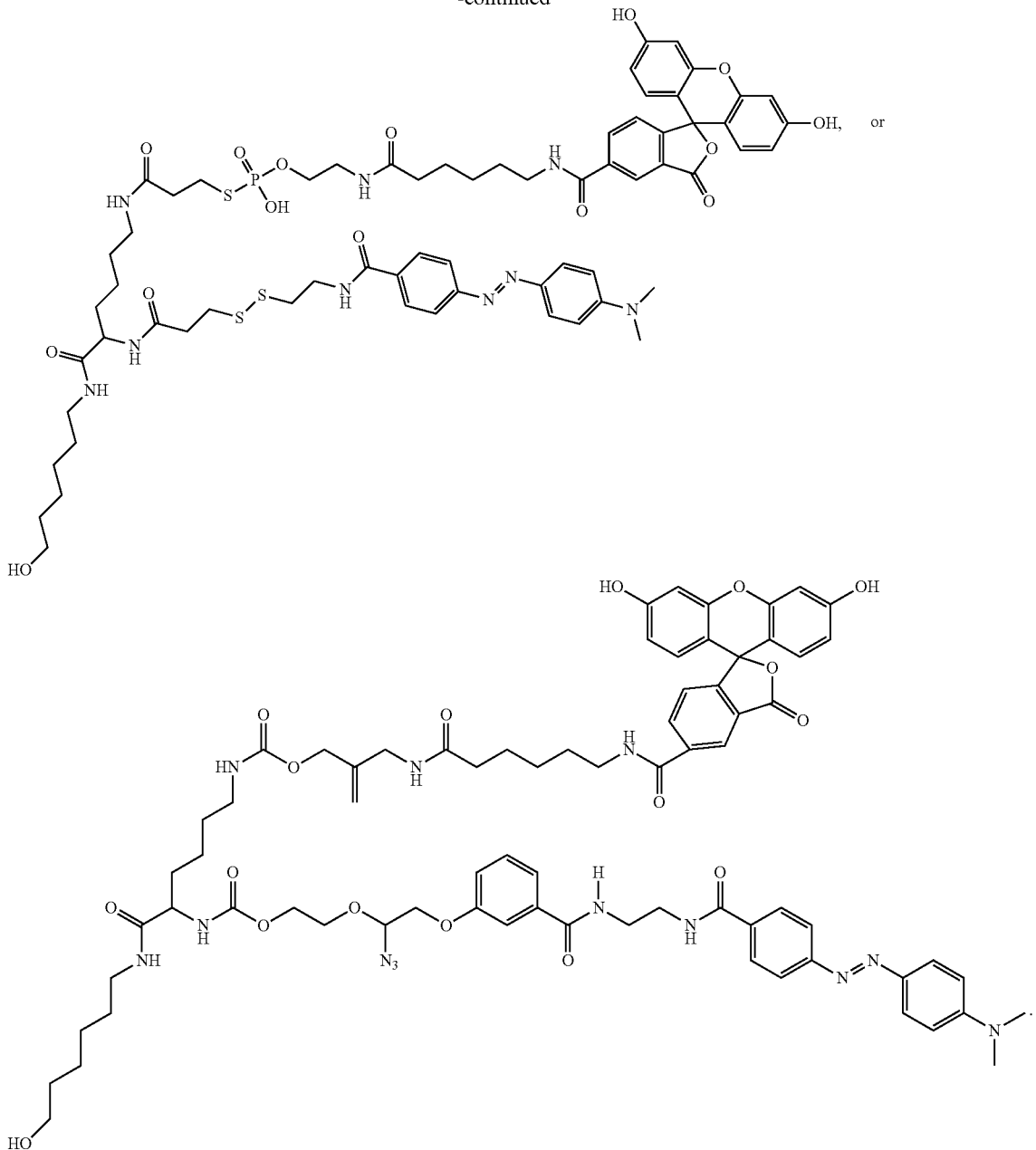

17. A method of detecting a target molecule, comprising:
contacting a sample suspected of containing the target molecule with a fluorochrome-quencher conjugate according to claim 1; and
measuring the fluorescence.

18. The method of claim 17, further comprising selectively cleaving the at least one first and/or the at least one second linker molecule prior to measuring the fluorescence, wherein cleavage is achieved by adding at least one selective cleavage reagent or incubating the sample under conditions that allow selective cleavage of the at least one first or the at least one second linker molecule.

19. A method of detecting two or more targets of interest, comprising:
contacting a sample suspected of containing the two or more targets of interest with two or more fluorochrome-quencher conjugates according to claim 1, wherein F and Q of each of the two or more fluorochrome-quencher conjugate are the same, wherein L1 and L2 of each of the two or more fluorochrome-quencher conjugate are different, and L2 is directly attached to Q via amide coupling; and
measuring the fluorescence.

20. The method of claim 19, further comprising selectively cleaving the at least one first and/or the at least one second linker molecule in each of the two or more fluorochrome-quencher conjugate prior to measuring the fluorescence, wherein cleavage is achieved by adding at least one selective cleavage reagent or incubating the sample under conditions that allow selective cleavage of the at least one first or the at least one second linker molecule of each of the two or more fluorochrome-quencher conjugate.

21. The conjugate of claim 1, wherein the at least one quenching molecule is Dabcyl.

22. The method of claim 17, wherein the fluorochrome-quencher comprises Dabcyl.

23. The method of claim 19, wherein Q is Dabcyl.

* * * * *